(12) United States Patent
Bodnar et al.

(10) Patent No.: US 12,740,701 B2
(45) **Date of Patent: *Sep. 22, 2026**

(54) DEVICES, SYSTEMS, AND METHODS TO MEASURE CORNEAL TOPOGRAPHY

(71) Applicant: Vision Labs, Inc., San Francisco, CA (US)

(72) Inventors: Zachary Bodnar, Las Vegas, NV (US); Jochen Kumm, Palo Alto, CA (US); Nikolai Steklov, Bakersfield, CA (US); Anatoli Trafimuk, Minsk (BY)

(73) Assignee: Vision Labs, Inc., Mill Valley, CA (US)

( * ) Notice: Subject to any disclaimer, the term of this patent is extended or adjusted under 35 U.S.C. 154(b) by 539 days.

This patent is subject to a terminal disclaimer.

(21) Appl. No.: 18/152,039

(22) Filed: Jan. 9, 2023

(65) Prior Publication Data

US 2023/0380682 A1 Nov. 30, 2023

Related U.S. Application Data

(63) Continuation of application No. PCT/US2021/041105, filed on Jul. 9, 2021.

(60) Provisional application No. 63/141,203, filed on Jan. 25, 2021, provisional application No. 63/049,631, filed on Jul. 9, 2020.

(51) Int. Cl.
*A61B 3/14* (2006.01)
*A61B 3/107* (2006.01)

(52) U.S. Cl.
CPC .................................... *A61B 3/107* (2013.01)

(58) Field of Classification Search
CPC .............................. A61B 3/107; A61B 3/0025
USPC .................................................. 351/206, 212
See application file for complete search history.

(56) References Cited

U.S. PATENT DOCUMENTS

| | | |
|---|---|---|
| 5,108,960 A | 4/1992 | Boek et al. |
| 6,322,216 B1 | 11/2001 | Yee et al. |
| 2002/0192445 A1 | 12/2002 | Ezzell et al. |
| 2003/0144650 A1 | 7/2003 | Smith |
| 2008/0247170 A1 | 10/2008 | Peck |
| 2013/0201451 A1 | 8/2013 | Simonov et al. |
| 2014/0049748 A1 | 2/2014 | Hee |
| 2016/0001496 A1 | 1/2016 | Chow et al. |
| 2016/0198946 A1 | 7/2016 | Zhou |
| 2017/0042421 A1 | 2/2017 | Wallace et al. |
| 2017/0127045 A1 | 5/2017 | Lin et al. |
| 2017/0172406 A1 | 6/2017 | Pamplona et al. |

(Continued)

FOREIGN PATENT DOCUMENTS

| | | |
|---|---|---|
| CN | 102869299 A | 1/2013 |
| CN | 107529983 A | 1/2018 |

(Continued)

OTHER PUBLICATIONS

PCT/US2021/041105 International Search Report and Written Opinion dated Dec. 16, 2021.

(Continued)

*Primary Examiner* — Mahidere S Sahle
(74) *Attorney, Agent, or Firm* — Wilson Sonsini Goodrich & Rosati

(57) ABSTRACT

Provided are devices, systems, and methods configured to uniformly illuminate a biological sample with a patterned illumination source and determine a contour of the biological sample.

20 Claims, 19 Drawing Sheets

(56) References Cited

U.S. PATENT DOCUMENTS

| | | | | |
|---|---|---|---|---|
| 2018/0092534 | A1 | 4/2018 | Nabhan | |
| 2018/0249905 | A1* | 9/2018 | Farrer | A61B 3/14 |
| 2019/0307325 | A1 | 10/2019 | Eil et al. | |
| 2021/0401282 | A1* | 12/2021 | Limon | A61B 3/032 |

FOREIGN PATENT DOCUMENTS

| | | | |
|---|---|---|---|
| KR | 20190097032 | A | 8/2019 |
| WO | WO-2002090452 | A2 | 11/2002 |
| WO | WO-2011139148 | A1 | 11/2011 |
| WO | WO-2019001928 | A1 | 1/2019 |
| WO | WO-2022011273 | A1 | 1/2022 |
| WO | WO-2025081166 | A1 | 4/2025 |

OTHER PUBLICATIONS

Pătrăucean et al. A parameterless line segment and elliptical arc detector with enhanced ellipse fitting. Fitzgibbon et al. (Eds.): ECCV 2012, Part II, Lecture Notes in Computer Science, vol. 7573, pp. 572-585, 2012.

EP20210837763.8 Extended European Search Report dated Jul. 8, 2024.

CN202180061638.4 Office Action with Search Report dated Mar. 13, 2026, and an English translation.

Co-pending U.S. Appl. No. 19/642,349, inventors Steklov; Nikolai et al., filed Apr. 8, 2026.

PCT/US2024/051283 International Search Report and Written Opinion dated Dec. 19, 2024.

* cited by examiner

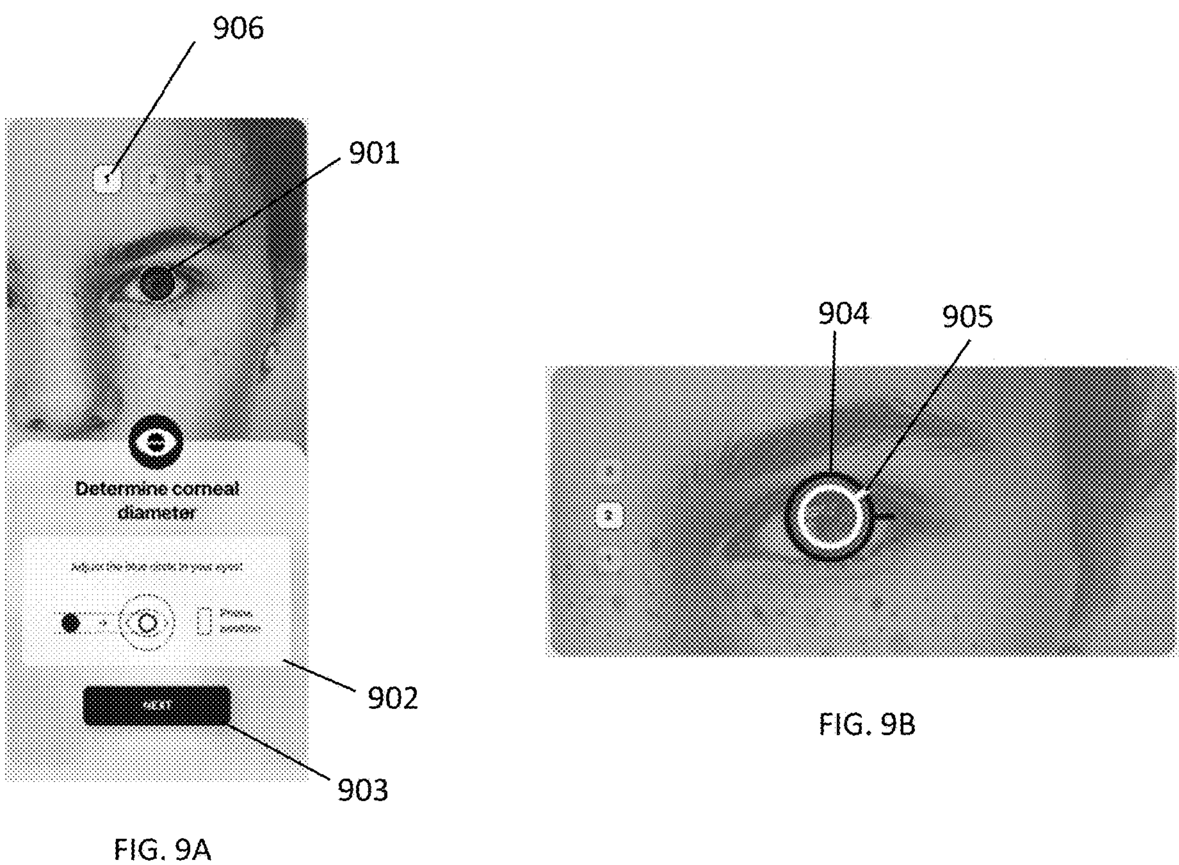
FIG. 9A
FIG. 9B
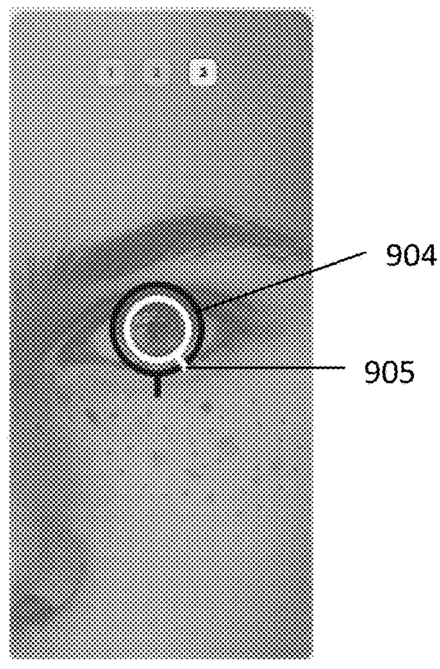
FIG. 9C

1100

DEVICES, SYSTEMS, AND METHODS TO MEASURE CORNEAL TOPOGRAPHY

CROSS-REFERENCE

This application is a continuation of International Patent Application No. PCT/US2021/041105, filed Jul. 9, 2021, which claims priority to U.S. Provisional Application No. 63/049,631, filed Jul. 9, 2020, and U.S. Provisional Application No. 63/141,203, filed Jan. 25, 2021, each of which is incorporated herein by reference in its entirety for all purposes.

BACKGROUND

Corneal topography has become a valuable diagnostic parameter for routine eye examination, pre-operative planning and evaluation for laser refractive surgeries (e.g., LASIK and PRK), contact lens fitting, evaluation of cataract and numerous corneal diseases such as keratoconus. Commercially available corneal topography systems (i.e., keratometers) are typically complex, expensive bench top systems located at offices of corneal specialists, laser vision correction surgeons, cataract surgeons, and eye care professionals (e.g., ophthalmologists or optometrists) whom frequently measure the corneal topography of their patients. Unfortunately, the relatively high cost of these systems ($8,000 to over $50,0000) and the need of specially trained medical personal preclude the wide-spread use of keratometry for healthcare professionals located in rural and resource limited areas. In such rural areas, patients in need of an eye examination to measure their corneal topography would need to travel to the nearest large town or city that may not be feasible or convenient for repeat or follow up visits if necessary. Enabling local general practitioner physicians in rural and low resource communities to screen their patient's corneal topographies would circumvent such inefficiencies and provide rapid screening and accessibility to local longitudinal monitoring of their corneal disease. Therefore, there exists an unmet need of a rapid, low-cost point-of-care system and device configured to measure and monitor corneal topography without the need of costly equipment and specialized medical personnel.

SUMMARY

Provided herein are apparatuses, systems and methods of their use that can measure the corneal topography of a subject's cornea at the point-of-care without the need of expensive keratometry equipment or specially trained medical personnel. In one aspect, the low-cost aspect may be achieved by the use of a common smart phone to emit, detect and process light signals to determine the corneal topography of a subject's cornea. In another aspect, a low-cost light source may couple to a smart phone to detect and process reflected light signals. By providing low-cost, user-friendly point-of-care apparatuses, systems and methods to measure corneal topography a larger patient population may, for example, undergo frequent screening of corneal topography to monitor and prevent the progression of corneal diseases (e.g., keratoconus) that would otherwise only seek medical care once symptoms present.

Aspects disclosed herein provide an apparatus for corneal topography measurement, comprising: a panel configured to releasably couple to a mobile device, wherein the panel is further configured to (a) project a light pattern onto a cornea of an eye to generate a reflected light pattern and (b) aid transmission of the reflected light pattern from the cornea to an imaging device on the mobile device for generating a plurality of light signals, wherein an optical axis of the imaging device is offset from (i) a patterned region or (ii) an illumination source on the panel. In some embodiments, the offset between the optical axis of the imaging device and the pattern region or the illumination source on the panel is from about 1 mm to about 10 mm. In some embodiments, the offset between the optical axis of the imaging device and the pattern region or the illumination source on the panel is from about 5 to about 360 degrees. In some embodiments, the panel is configured to serve as a protective casing for the mobile device. In some embodiments, the panel light pattern comprises a plurality of lines. In some embodiments, the plurality of lines is linear. In some embodiments, the plurality of lines is circular or radial. In some embodiments, the panel comprises a quick release mechanism that enables the panel to be releasably coupled to the mobile device. In some embodiments, the plurality of lines is provided on a surface of the panel. In some embodiments, the panel is transparent or translucent. In some embodiments, the panel has an absorption coefficient of at least 1 cm^−1. In some embodiments, the plurality of lines is opaque.

Aspects disclosed herein provide a system comprising: the apparatus previously described; and one or more processors configured to process the plurality of light signals by (i) comparing the projected light pattern to the reflected light pattern to produce a two-dimensional elevation gradient, and (ii) using the two-dimensional elevation gradient to generate a three-dimensional topographic map of the cornea. In some embodiments, the one or more processors are located on the mobile phone. In some embodiments, the one or more processors are located on a server remote from the mobile device. In some embodiments, the system further comprises the mobile device, and wherein the mobile device comprises a depth sensor configured to measure a distance from the cornea to the imaging device.

Aspects disclosed herein provide a method of measuring corneal topography, comprising: (a) providing a panel having a plurality of lines; (b) coupling the panel to a mobile device in a configuration such that an optical axis of the imaging device is offset from a patterned region on the panel or an illumination source on the panel; (c) placing the panel coupled to the mobile device in proximity to an eye of a subject; (d) using the panel and the illumination source to project a light pattern onto the cornea to generate a reflected light pattern; (e) using the imaging device on the mobile device to receive the reflected light pattern to generate a plurality of light signals; and (f) generating a topography map of the cornea based at least in part on the plurality of light signals. In some embodiments, (e) further comprises using a depth sensor on the mobile device to detect a distance between the panel and the eye of the subject. In some embodiments, the plurality of lines on the panel are linear. In some embodiments, the plurality of lines on the panel are circular or radial. In some embodiments (e) further comprises rotating the imaging device as the imaging device is receiving the reflected light pattern.

Aspects disclosed herein provide an apparatus for illuminating a target, comprising: a first surface comprising a plurality of light scattering elements and a second surface comprising a plurality of illumination elements in optical communication with the plurality of light scattering elements, wherein the first surface comprises a light inlet comprising a curved surface or waveguide configured to (i) receive light emitted from a light source and (ii) direct the light to the plurality of light scattering elements, wherein the plurality of light scattering elements is configured to transmit the light to the plurality of illumination elements, and wherein the plurality of illumination elements is configured to generate an illumination pattern for illuminating the target. In some embodiments, the plurality of light scattering elements comprises one or more dome reflectors, scattering particles, or any combination thereof. In some embodiments, the curved surface or waveguide is configured to receive and distribute the light from the light source to the plurality of light scattering elements while reducing or minimizing a light hot spot at or near the light inlet or the light source. In some embodiments, the light hot spot corresponds to a concentration of light at or near the light inlet. In some embodiments, the second surface comprises a reflective coating. In some embodiments, the plurality of illumination elements is spatially arranged in a predetermined pattern. In some embodiments, the plurality of illumination elements comprises a linear shape. In some embodiments, the plurality of illumination elements comprises a non-linear shape. In some embodiments, the non-linear shape comprises a curve or an arc. In some embodiments, the plurality of light scattering elements comprises a two-dimensional array of light scattering elements arranged on the first surface. In some embodiments, the illumination elements comprise one or more surfaces for illuminating the target or directing light to the target. In some embodiments, the two-dimensional array comprises a linear configuration, non-linear linear configuration, or any combination thereof. In some embodiments, the apparatus further comprises an optically transparent window in optical communication with the light source. In some embodiments, the light source comprises a light emitting diode (LED). In some embodiments, the light source is located on a mobile device. In some embodiments, the apparatus comprises a panel that is configured to serve as a protective casing for a mobile device. In some embodiments, the panel comprises a quick release mechanism that enables the panel to be releasably coupled to the mobile device. In some embodiments, the illumination pattern generated by the plurality of illumination elements is configured to provide a uniform illumination. In some embodiments, the uniform illumination comprises an illumination of one or more regions of the target such that a first region of the target has a brightness that is within 10% of brightness of a second region of the target. In some embodiments, the uniform illumination comprises an illumination of one or more regions of the target such that a first region of the target has a brightness that is within 0% of brightness of a second region of the target. In some embodiments, the uniform illumination comprises an illumination of one or more regions of the target such that a first region of the target has a same or similar brightness as a second region of the target. In some embodiments, the target comprises a biological tissue. In some embodiments, the biological tissue is a mammalian cornea. In some embodiments, the quick release mechanism comprises a snap-fit.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 9A-9C illustrate a graphical user interface and image overlay of a mobile phone application capable of guiding a subject through measuring the diameter of the subject's cornea and measuring the subject's corneal topography, in accordance with some embodiments.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Corneal topographic measurements can provide a rich dataset of diagnostic and prognostic factors that could greatly impact a subject's quality of life. For example, a subject interested in contact lenses can have their corneal curvature measured by keratometry to ensure proper fit and function of the contact lens. Without proper measurement of a subject's cornea and fit of a contact lens, the subject may exhibit blurry vision or pain and potential damage to the subject's eye. Additionally, corneal topographic measurements can also be used as a preventative diagnostic screening tool or to monitor corneal surgical outcomes. In some embodiments, the methods of measuring corneal topography disclosed herein may be used to determine the optimal fit or function for contact lenses. In some embodiments, the methods of measuring corneal topography disclosed herein may be used to diagnose, monitor or screen corneal conditions, corneal diseases, pre-operative corneal structure or post-operative changes in corneal structure. Examples of corneal conditions or disease may comprise corneal keratoconus, ectasia, pterygium formation, limbal dermoid formation or any combination thereof. In some embodiments, pre-operative corneal structure may be analyzed using the systems or methods herein, prior to using laser assisted in situ keratomileusis (LASIK) to perform LASIK corneal corrective procedures. In some embodiments, post-operative corneal structure may be analyzed using the systems or methods herein, after LASIK surgery to monitor corneal healing and the resulting change in corneal topography over time.

In some instances, the non-invasive measure of corneal topography by a costly keratometer can limit the availability and frequency by which subjects are able to monitor corneal curvature. Therefore, the present invention disclosed herein can address this shortcoming by providing systems, methods, and apparatuses to measure corneal topography and curvature at the point-of-care.

I. Local and Cloud-Based System

Figure 1:
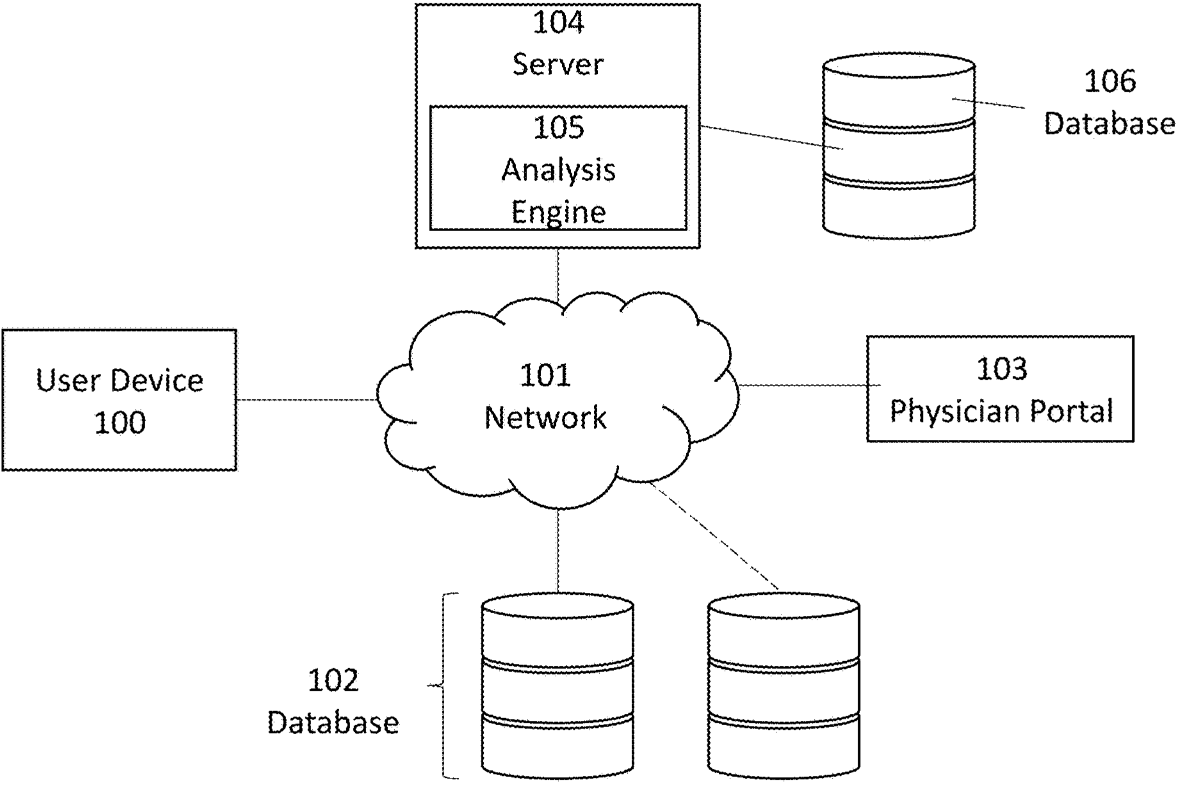
FIG. 1 illustrates a cloud base system workflow for a point-of-care device configured to measure corneal topographical and reporting such measurements to a physician remotely, in accordance with some embodiments.
Figure 2:
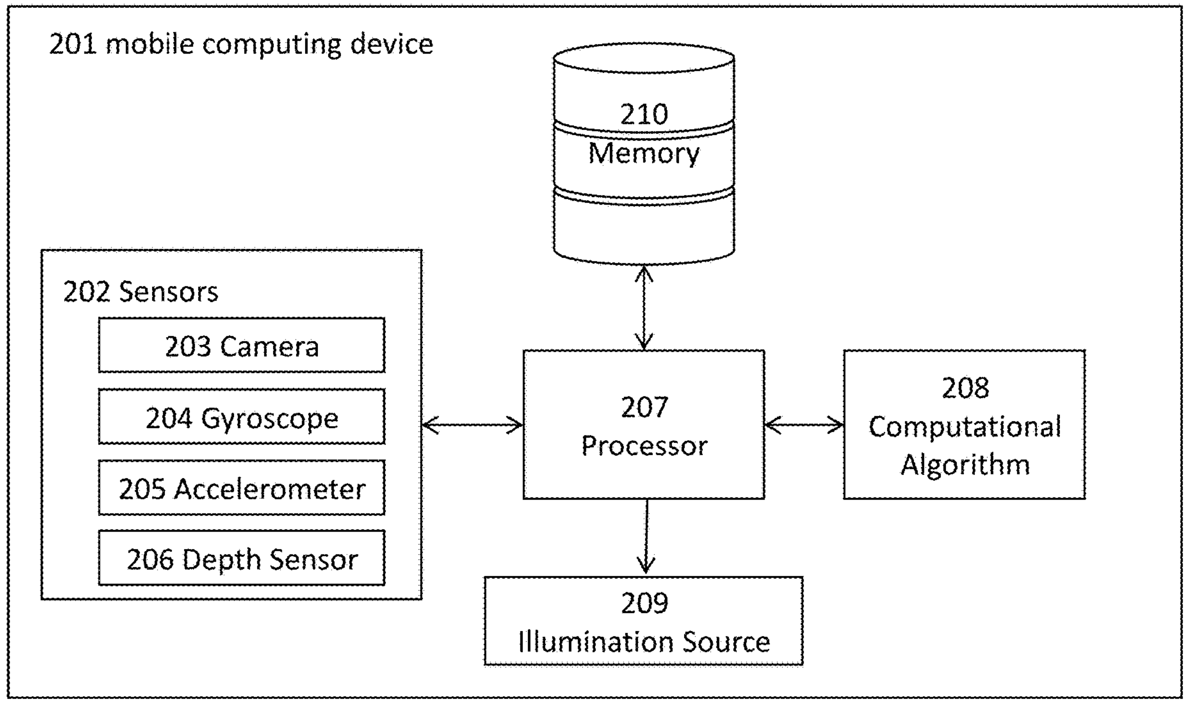
FIG. 2 shows a device system workflow for a point-of-care corneal topography measurement user device configured to measure corneal topography off-line, in accordance with some embodiments.

Aspects disclosed herein provide systems, methods and apparatuses, in some embodiments, that may operate locally off-line or on a cloud-based platform, as seen in FIG. 1. In some embodiments, the illumination, acquisition, image processing, and data storage may occur locally on a subject's mobile computing device as seen in FIG. 2. In some embodiments, image illumination and acquisition may be completed locally on a subject's mobile computing device 100 and image processing and analysis 105 completed on a remote server 104 through the network 101, as can be seen in FIG. 1. In some embodiments, the subject's data may also be stored in a remote HIPPA compliant database 102 that would interface with both the analysis engine 105 and a physician portal 103 through a cloud-based network 101. In some embodiments, the server 104 may comprise one or more processors that can process a subject's corneal reflected light pattern images. In some embodiments, medical personnel may remotely access a subject's corneal topographical data remotely through the physician portal 103. In some embodiments, the physician portal 103 may permit medical personnel to send recommendations and communications after viewing patient corneal data. In some embodiments, the medical personnel may complete further analysis on a subject's corneal reflected light pattern images on demand using the analysis engine 105 remotely through the network 101. In some embodiments, the analysis engine 105 may comprise a plurality of processing algorithms. In some embodiments, the plurality of processing algorithms may comprise processes for denoising, segmenting, deblurring, distortion correction, correction of chromatic aberration and extracting corneal topography from a plurality of corneal reflected light pattern images. In some embodiments, analysis engine 105, server 104 and database 106 may provide longitudinal processing and monitoring of a subject's corneal topographical data over time. In some embodiments, the longitudinal monitoring may be presented to medical personnel in an intuitive graphical user interface on the physician portal 103. In some embodiments, the cloud-based system shown in FIG. 1 may be integrated with pre-existing electronic medical record systems (EMR).

In some embodiments, the mobile computing device may comprise an onboard system configured to illuminate, measure, orient, process or store a subject's corneal topographic measurements as can be seen in FIG. 2. In some embodiments, the onboard system may comprise one or more processors 207 in electrical communication with a plurality of sensors 202, onboard memory 210, computational algorithm 208 or any combination thereof. In some embodiments, the plurality of sensors 202 may comprise a camera 203, gyroscope 204, accelerometer 205, depth sensor 206 or any combination thereof. In some embodiments, the camera may be a CMOS visible light camera sensitive to radiative energy in the visible spectrum. In some embodiments, the camera 203 may be a CCD visible light camera sensitive to radiative energy in the visible spectrum. In some embodiments, the camera 203 may be sensitive to radiative energy in the near-infrared spectrum. In some embodiments, the computational algorithm 208 may comprise algorithms to segment portions of captured image data, filtering and de-noising image data, measure size parameters of the segmented objects or any combination thereof. In some embodiments, the size parameters measured may comprise diameter, area, length, width, distance, circumference or any combination thereof. In some embodiments, segmentation algorithms may comprise manual segmentation, ellipse and line segmentation, Hough transform, color segmentation or any combination thereof. In some embodiments, segmentation may segment regions of captured image data by similar local pixel neighborhood gradients. In some embodiments, the local pixel neighborhood gradients will be aligned with one another to generate segments of smooth pixel clusters. In some embodiments, neighboring smooth pixel clusters may be combined together to generate closed contour segments. In some embodiments, the computational algorithm 208 may comprise algorithms to calculate elevation using methods described elsewhere herein of reflected illumination pattern off of a subject's cornea. In some embodiments, the computational algorithm 208 may comprise image processing functions of denoising, blurring, smoothing, binarization or any combination thereof. In some embodiments, the computational algorithms may measure the length, width, distance or any combination thereof the reflected illumination pattern from the cornea to measure a given topography at a given meridian. In some embodiments, the computational algorithm 208 may comprise a highly parallel computational structure executed on one or more parallel processors 207. In some embodiments, the highly parallel computational structure may comprise a plurality of processing cores that each may comprise a plurality of threads. In some embodiments, a first thread of a plurality of threads may be configured to execute a function simultaneously with a second thread of a plurality of threads. In some embodiments, a thread may perform a process, for example, image acquisition, pattern illumination, image segmentation, image processing or any combination thereof. In some embodiments, the computational algorithm may comprise a highly parallel computation structure executed on a graphical processing unit (GPU). In some embodiments, a subject's corneal topographic information may be stored locally in memory 210 until further processing or sharing with clinical personnel. In some embodiments, a subject's corneal topographic information may be transmitted via the network 101 and stored in a cloud database 102. In some embodiments, the memory 210 may be encrypted to store personal health information (PHI) compliant under the health insurance portability and accountability act (HIPPA). In some embodiments, the PHI compliant under HIPPA may be uploaded to an electronic medical record system (EMR) for further review by clinical personnel.

II. Measurement of Corneal Diameter and Topography

Systems and methods are provided herein for calculating a subject's corneal diameter and topography. Aspects of the present disclosure, in some embodiments, provide a method of determining a subject's corneal diameter by scale, geometric optics or any combination thereof. Further aspects of the present disclosure may then determine corneal topography by combining the measured corneal diameter in combination with a deviation of a captured reflected signal of an illumination pattern of known size and shape.

In some embodiments, the diameter of the subject's cornea may be determined by geometric optics and ray tracing between the object (e.g., a subject's cornea) and the imaging system components. In some embodiments determining the subject's corneal diameter by geometric optics and ray tracing may depend on the diameter of the cornea in pixels of an imaging sensor, the resolution of the captured image in pixels/unit length, the distance between the subject's corneal limbus and the imaging sensor's field of view. In some embodiments, the subject's corneal diameter in pixels may be determined by capturing an image of the subject's cornea with an imaging sensor with a defined number of pixels. In some embodiments, the imaging sensor may comprise a pixel size of about 1 μm to about 10 μm. In some embodiments, the imaging sensor may comprise a pixel size of about 1 μm to about 2 μm, about 1 μm to about 3 μm, about 1 μm to about 4 μm, about 1 μm to about 5 μm, about 1 μm to about 6 μm, about 1 μm to about 7 μm, about 1 μm to about 8 μm, about 1 μm to about 9 μm, about 1 μm to about 10 μm, about 2 μm to about 3 μm, about 2 μm to about 4 μm, about 2 μm to about 5 μm, about 2 μm to about 6 μm, about 2 μm to about 7 μm, about 2 μm to about 8 μm, about 2 μm to about 9 μm, about 2 μm to about 10 μm, about 3 μm to about 4 μm, about 3 μm to about 5 μm, about 3 μm to about 6 μm, about 3 μm to about 7 μm, about 3 μm to about 8 μm, about 3 μm to about 9 μm, about 3 μm to about 10 μm, about 4 μm to about 5 μm, about 4 μm to about 6 μm, about 4 μm to about 7 μm, about 4 μm to about 8 μm, about 4 μm to about 9 μm, about 4 μm to about 10 μm, about 5 μm to about 6 μm, about 5 μm to about 7 μm, about 5 μm to about 8 μm, about 5 μm to about 9 μm, about 5 μm to about 10 μm, about 6 μm to about 7 μm, about 6 μm to about 8 μm, about 6 μm to about 9 μm, about 6 μm to about 10 μm, about 7 μm to about 8 μm, about 7 μm to about 9 μm, about 7 μm to about 10 μm, about 8 μm to about 9 μm, about 8 μm to about 10 μm, or about 9 μm to about 10 μm. In some embodiments, the imaging sensor may comprise a pixel size of about 1 μm, about 2 μm, about 3 μm, about 4 μm, about 5 μm, about 6 μm, about 7 μm, about 8 μm, about 9 μm, or about 10 μm. In some embodiments, the imaging sensor may comprise a pixel size of at least about 1 μm, about 2 μm, about 3 μm, about 4 μm, about 5 μm, about 6 μm, about 7 μm, about 8 μm, or about 9 μm. In some embodiments, the imaging sensor may comprise a pixel size of at most about 2 μm, about 3 μm, about 4 μm, about 5 μm, about 6 μm, about 7 μm, about 8 μm, about 9 μm, or about 10 μm.

In some embodiments, the corneal diameter in pixels from the captured image may be extracted by image processing methods of segmentation. In some embodiments, segmentation methods may comprise segmentation by intensity thresholding, gradient thresholding, canny edge detection, sobel edge detection, Hough transform, ellipse and line segment detector (ELSD) or any combination thereof. Once the shape of the cornea is segmented, the diameter of the cornea, in some embodiments may be determined by dividing the area of the cornea in a plurality of parallel horizontal and vertical line segments across the entirety of the segmented corneal area. In some embodiments, the average of the longest length of the vertical and horizontal line segments may indicate the diameter of the subject's cornea in pixels. In addition to the diameter of the subject's cornea in pixels, the distance between the imaging sensor and the corneal limbus may be determined to measure the diameter of the subject's cornea.

The corneal limbus is defined as the plane between the cornea (the translucent or transparent region of an eye) and the sclera (the white region of an eye). In some embodiments, the distance between the imaging sensor and the corneal limbus may be determined by a depth sensor. In some embodiments, the depth sensor may comprise a light detection and ranging (LiDAR), time of flight (TOF) sensors or any combination thereof. In some embodiments, the distance between the camera imaging plane and corneal limbus may be determined by a stereoscopic imaging system comprising two or more imaging sensors separated by an angle, a distance or any combination thereof.

In some embodiments, a geometric optics mathematical relationship combining the diameter of a subject's cornea in pixels of an imaging sensor, the imaging sensors angular field, the distance between the imaging sensor plane and the cornea limbus and the resolution of a captured image in pixels/unit length may be used to determine the diameter of the subject's cornea. For example, the diameter of the cornea may be shown by the following equation:

$$d = \frac{2d'z}{w}\tan\left(\frac{\varphi}{2}\right)$$

Where d is the diameter of the cornea, d' is the diameter of the cornea in pixels, φ is the angular field of view of the camera sensor, w is the resolution of the captured image in pixels/unit length, and z is the distance between the camera sensor to the corneal limbus.

In some embodiments, the diameter of the cornea may be determined by a method of scale. In some embodiments, the method of determining corneal diameter by scale includes the steps of: (1) placing a fiducial marker of known size adjacent to a subject's cornea; (2) capturing an image of the cornea and adjacent fiducial marker; (3) segmenting the fiducial marker from the image; (4) determining the image pixel resolution of the image from the known scale of the fiducial marker; (5) segmenting the cornea from the image; (6) determining the diameter of the segmented cornea from the calculated image pixel resolution. In some embodiments, the segmentation of the fiducial marker and cornea may be achieved by segmentations methods disclosed previously herein. In some embodiments, the fiducial marker may be circular, square, rectangular, trapezoidal, triangular, ellipsoid or other regular or irregular polygonal in shape. In some embodiments, the fiducial marker may be patterned, colored, textured or any combination thereof.

Figures 3A, 3B:
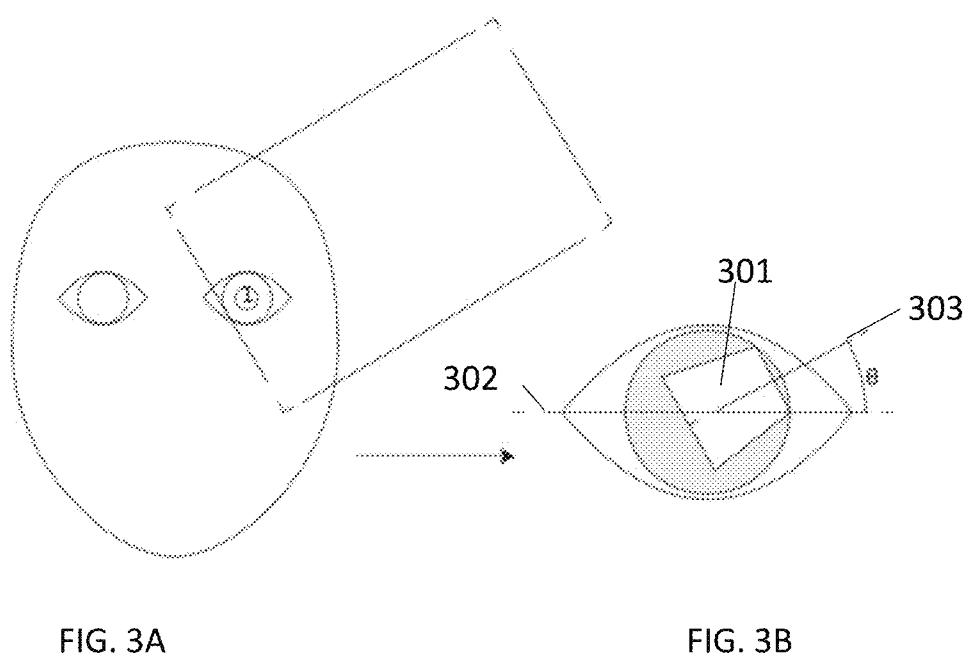
FIGS. 3A-3B illustrate a method for determining corneal curvature along a specific axis, in accordance with some embodiments.
Figure 5A:
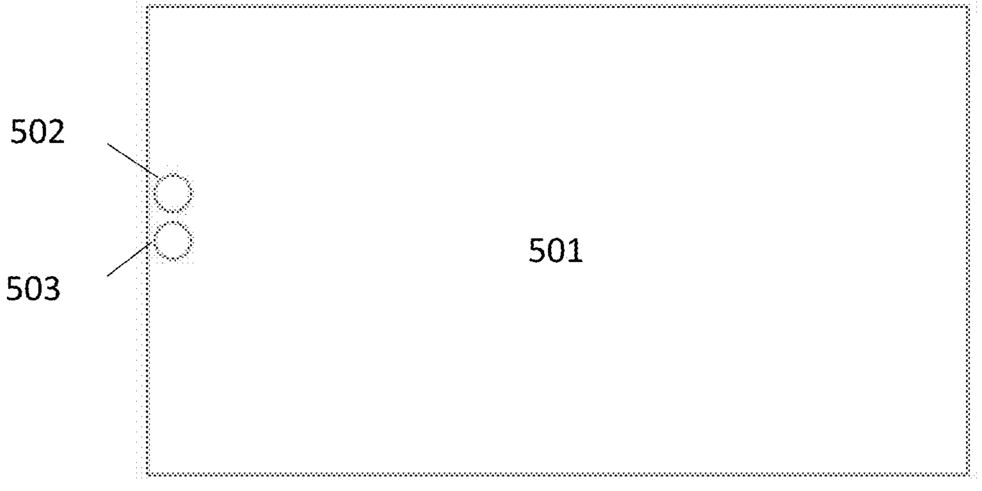
FIGS. 5A-5B illustrate the position and geometry of a light illumination pattern with respect to the corneal topography measurement apparatus camera and depth sensor, in accordance with some embodiments.
Figure 5B:

In some embodiments, corneal topography may be calculated by capturing the reflected light pattern off a subject's cornea by a light sensor. In some embodiments, the method of measuring corneal topography may comprise the steps of: (a) providing a panel 301, as seen in FIGS. 3A-3B having a plurality of lines 504 (FIG. 5B); (b) coupling the panel to a mobile device in a configuration such that an optical axis of the imaging device 503 (FIGS. 5A-5B) is offset from a patterned region on the panel or an illuminator source on the panel 504; (c) placing the panel coupled to the mobile device in proximity to an eye of a subject; (d) using the panel and the illumination source to project a light pattern onto the cornea to generate a reflected light pattern; (e) using the imaging device 503 on the mobile device to receive the reflected light pattern 1301, as seen in FIG. 14, to generate a plurality of light signals; and (f) generating a topography map of the cornea based at least in part on the plurality of light signals.

Figure 14:
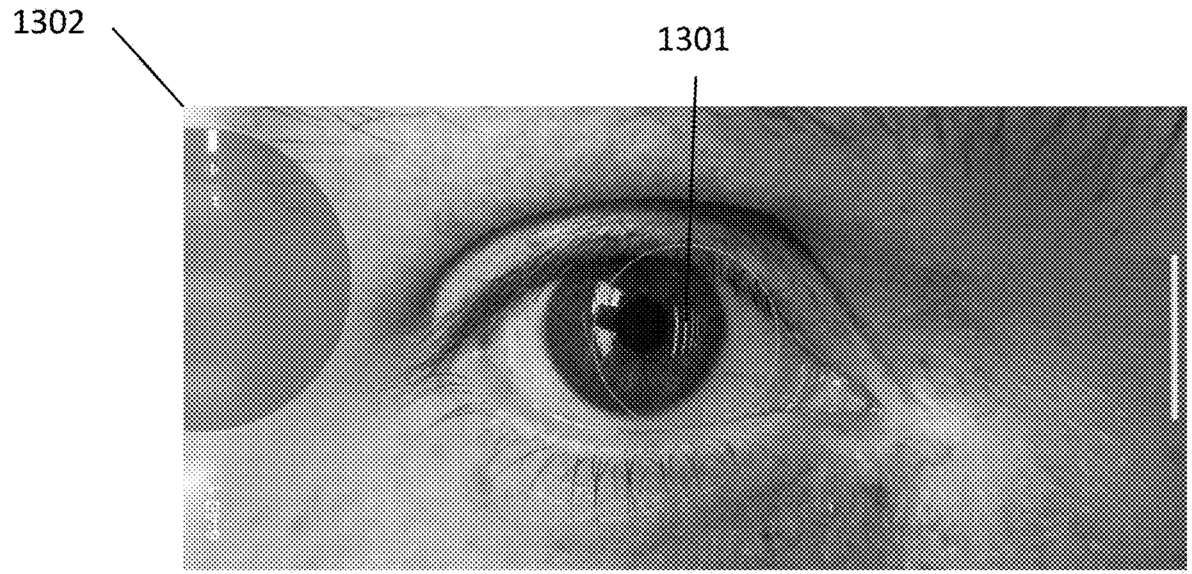
FIG. 14 shows an example corneal image highlighting the reflected illumination pattern on a subject's cornea used to determine corneal topography, in accordance with some embodiments.

In some embodiments, generating a topography map of the cornea can be achieved by a comparison of the known spacing of the illumination pattern source and the spacing of the received reflected light patterns off of a subject's cornea 1301, as can be seen in FIG. 14. In some embodiments, the imaging device can be rotated as the imaging device is receiving the reflected light pattern to generate a 3-D topography map of the corneal surface. In some embodiments, as the imaging device is rotated, the imaging device may acquire a series of single images. In some embodiments, as the imaging device is rotated, the imaging device may acquire a continuous stream of high-speed video. In some embodiments, the high-speed video may be up to about 30, about 60, about 100 or about 120 frames per second (fps). In some embodiments, as the device is rotated, the Euler angle with respect to the beginning of the series of images acquired may be recorded by the mobile device gyroscope and accelerometer. In some embodiments, the series of acquired images may then be stitched together along a meridian of the cornea corresponding to the Euler angle recorded during acquisition. In some embodiments, cross-correlation, gaussian blurring, median filtering or any combination thereof post processing may be used to smooth the stitched image.

Turning attention to FIGS. 3A-3B the orientation and of the illumination panel and mobile device, in some embodiments disclosed herein will be described. In some embodiments, the illumination panel as shown in FIG. 3A may comprise an imaging axis that is orthogonal to a subject's corneal normal. In some embodiments, as shown in FIG. 3B the illumination panel 301 may be at an angle theta 303 with respect to the horizontal axis of the subject's cornea 302. In some embodiments, the angle theta may be about 10 degrees to about 90 degrees. In some embodiments, the angle theta may be about 10 degrees to about 20 degrees, about 10 degrees to about 30 degrees, about 10 degrees to about 40 degrees, about 10 degrees to about 50 degrees, about 10 degrees to about 60 degrees, about 10 degrees to about 70 degrees, about 10 degrees to about 80 degrees, about 10 degrees to about 90 degrees, about 20 degrees to about 30 degrees, about 20 degrees to about 40 degrees, about 20 degrees to about 50 degrees, about 20 degrees to about 60 degrees, about 20 degrees to about 70 degrees, about 20 degrees to about 80 degrees, about 20 degrees to about 90 degrees, about 30 degrees to about 40 degrees, about 30 degrees to about 50 degrees, about 30 degrees to about 60 degrees, about 30 degrees to about 70 degrees, about 30 degrees to about 80 degrees, about 30 degrees to about 90 degrees, about 40 degrees to about 50 degrees, about 40 degrees to about 60 degrees, about 40 degrees to about 70 degrees, about 40 degrees to about 80 degrees, about 40 degrees to about 90 degrees, about 50 degrees to about 60 degrees, about 50 degrees to about 70 degrees, about 50 degrees to about 80 degrees, about 50 degrees to about 90 degrees, about 60 degrees to about 70 degrees, about 60 degrees to about 80 degrees, about 60 degrees to about 90 degrees, about 70 degrees to about 80 degrees, about 70 degrees to about 90 degrees, or about 80 degrees to about 90 degrees. In some embodiments, the angle theta may be about 10 degrees, about 20 degrees, about 30 degrees, about 40 degrees, about 50 degrees, about 60 degrees, about 70 degrees, about 80 degrees, or about 90 degrees. In some embodiments, the angle theta may be at least about degrees, about 20 degrees, about 30 degrees, about 40 degrees, about 50 degrees, about degrees, about 70 degrees, or about 80 degrees. In some embodiments, the angle theta may be at most about 20 degrees, about 30 degrees, about 40 degrees, about 50 degrees, about 60 degrees, about 70 degrees, about 80 degrees, or about 90 degrees. In some embodiments, the orientation of the illumination panel with respect to the cornea may be determined by onboard sensors of the mobile device comprising the illumination panel. In some embodiments, the onboard sensors may comprise an inertial gyroscopic sensor, accelerometer or any combination thereof.

Figure 4A:
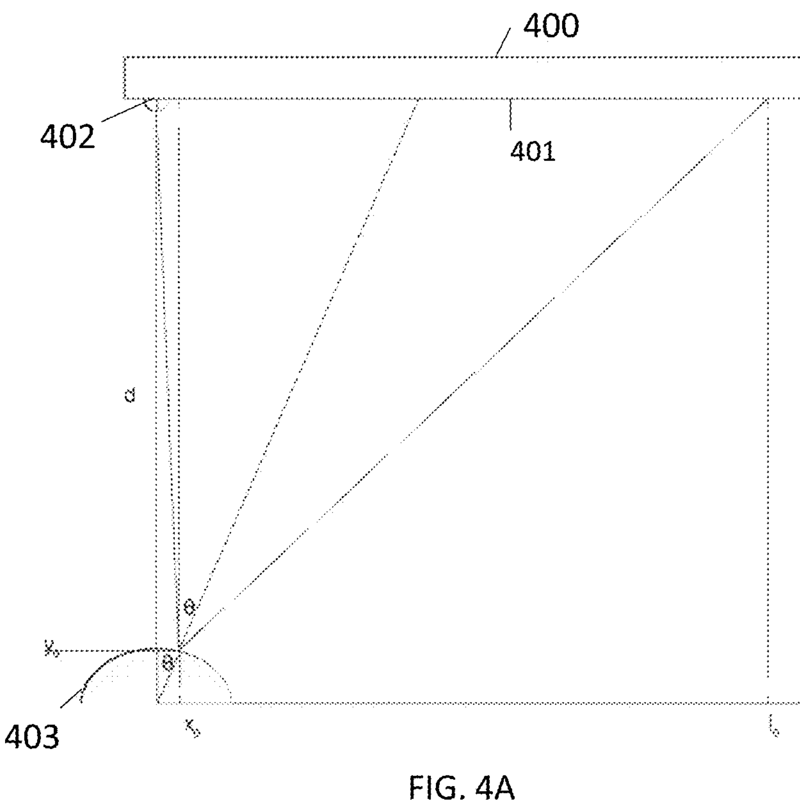
FIG. 4A illustrates the cross-sectional geometry utilized to estimate the elevation of the cornea at the reflection of the first source of the light illumination pattern.
Figure 4B:
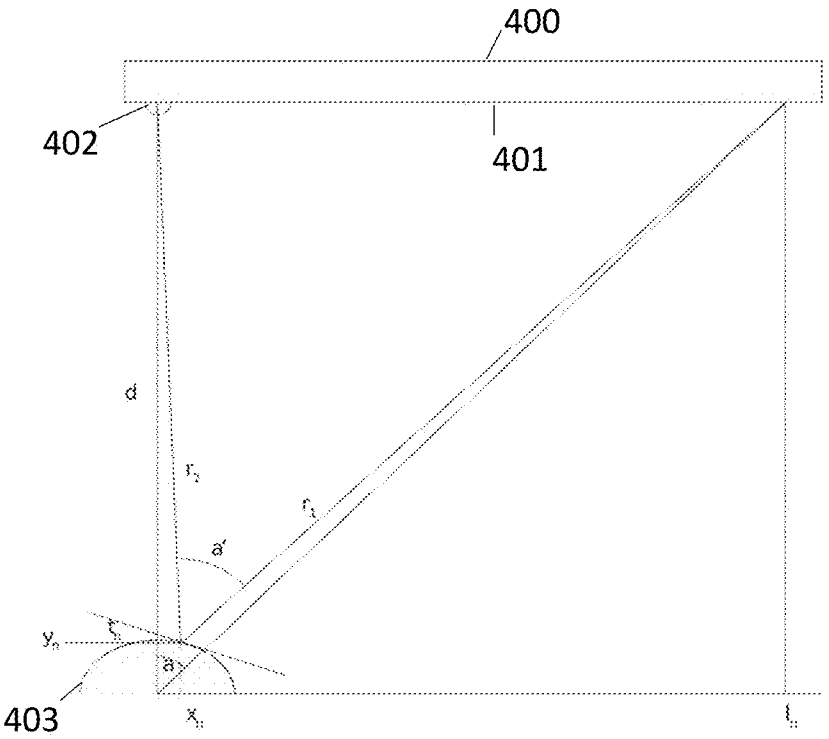
FIG. 4B illustrates the geometry used to estimate the elevation of the cornea at the reflection of sequential sources of the light illumination pattern, in accordance with some embodiments.

Referencing FIG. 4A-4B the geometry and relationship between the illumination panel 401, mobile computing device 400, camera sensor 402 and a subject's cornea 403 to calculate corneal topography are described next. In some embodiments, an illumination panel 401 comprising an illumination pattern may be projected onto the subject's cornea 403. In some embodiments, the pattern illumination may comprise parameters such as dimension, geometry, thickness, spacing, area or any combination thereof that are known a prior. The reflected illumination patterns off of the subject's cornea 403 may then be captured by the camera sensor 402 on the mobile computing device 400. In some embodiments, the deviation from the known parameters of the illumination pattern may be used to measure corneal topography.

In some embodiments, the illumination pattern may comprise a series of illumination sources. In some embodiments, the illumination sources may be at an offset with respect to the camera sensor 402. In some embodiments, the offset between the optical axis of the imaging device and the pattern region or the illumination source on the panel may be about 1 mm to about 10 mm. In some embodiments, the offset between the optical axis of the imaging device and the pattern region or the illumination source on the panel may be about 1 mm to about 2 mm, about 1 mm to about 3 mm, about 1 mm to about 4 mm, about 1 mm to about 5 mm, about 1 mm to about 6 mm, about 1 mm to about 7 mm, about 1 mm to about 8 mm, about 1 mm to about 9 mm, about 1 mm to about 10 mm, about 2 mm to about 3 mm, about 2 mm to about 4 mm, about 2 mm to about 5 mm, about 2 mm to about 6 mm, about 2 mm to about 7 mm, about 2 mm to about 8 mm, about 2 mm to about 9 mm, about 2 mm to about 10 mm, about 3 mm to about 4 mm, about 3 mm to about 5 mm, about 3 mm to about 6 mm, about 3 mm to about 7 mm, about 3 mm to about 8 mm, about 3 mm to about 9 mm, about 3 mm to about 10 mm, about 4 mm to about 5 mm, about 4 mm to about 6 mm, about 4 mm to about 7 mm, about 4 mm to about 8 mm, about 4 mm to about 9 mm, about 4 mm to about 10 mm, about 5 mm to about 6 mm, about 5 mm to about 7 mm, about 5 mm to about 8 mm, about 5 mm to about 9 mm, about 5 mm to about mm, about 6 mm to about 7 mm, about 6 mm to about 8 mm, about 6 mm to about 9 mm, about 6 mm to about 10 mm, about 7 mm to about 8 mm, about 7 mm to about 9 mm, about 7 mm to about 10 mm, about 8 mm to about 9 mm, about 8 mm to about 10 mm, or about 9 mm to about 10 mm. In some embodiments, the offset between the optical axis of the imaging device and the pattern region or the illumination source on the panel may be about 1 mm, about 2 mm, about 3 mm, about 4 mm, about 5 mm, about 6 mm, about 7 mm, about 8 mm, about 9 mm, or about 10 mm. In some embodiments, the offset between the optical axis of the imaging device and the pattern region or the illumination source on the panel may be at least about 1 mm, about 2 mm, about 3 mm, about 4 mm, about 5 mm, about 6 mm, about 7 mm, about 8 mm, or about 9 mm. In some embodiments, the offset between the optical axis of the imaging device and the pattern region or the illumination source on the panel may be at most about 2 mm, about 3 mm, about 4 mm, about 5 mm, about 6 mm, about 7 mm, about 8 mm, about 9 mm, or about 10 mm.

In some embodiments, the offset between the optical axis of the imaging device and the pattern region or the illumination source on the panel may be about 5 degrees to about 360 degrees. In some embodiments, the offset between the optical axis of the imaging device and the pattern region or the illumination source on the panel may be about 5 degrees to about 40 degrees, about 5 degrees to about 80 degrees, about 5 degrees to about 120 degrees, about 5 degrees to about 160 degrees, about 5 degrees to about 200 degrees, about 5 degrees to about 240 degrees, about 5 degrees to about 280 degrees, about 5 degrees to about 320 degrees, about 5 degrees to about 360 degrees, about 40 degrees to about 80 degrees, about 40 degrees to about 120 degrees, about 40 degrees to about 160 degrees, about 40 degrees to about 200 degrees, about 40 degrees to about 240 degrees, about 40 degrees to about 280 degrees, about 40 degrees to about 320 degrees, about 40 degrees to about 360 degrees, about 80 degrees to about 120 degrees, about 80 degrees to about 160 degrees, about 80 degrees to about 200 degrees, about 80 degrees to about 240 degrees, about 80 degrees to about 280 degrees, about 80 degrees to about 320 degrees, about 80 degrees to about 360 degrees, about 120 degrees to about 160 degrees, about 120 degrees to about 200 degrees, about 120 degrees to about 240 degrees, about 120 degrees to about 280 degrees, about 120 degrees to about 320 degrees, about 120 degrees to about 360 degrees, about 160 degrees to about 200 degrees, about 160 degrees to about 240 degrees, about 160 degrees to about 280 degrees, about 160 degrees to about 320 degrees, about 160 degrees to about 360 degrees, about 200 degrees to about 240 degrees, about 200 degrees to about 280 degrees, about 200 degrees to about 320 degrees, about 200 degrees to about 360 degrees, about 240 degrees to about 280 degrees, about 240 degrees to about 320 degrees, about 240 degrees to about 360 degrees, about 280 degrees to about 320 degrees, about 280 degrees to about 360 degrees, or about 320 degrees to about 360 degrees. In some embodiments, the offset between the optical axis of the imaging device and the pattern region or the illumination source on the panel may be about 5 degrees, about 40 degrees, about 80 degrees, about 120 degrees, about 160 degrees, about 200 degrees, about 240 degrees, about 280 degrees, about 320 degrees, or about 360 degrees. In some embodiments, the offset between the optical axis of the imaging device and the pattern region or the illumination source on the panel may be at least about 5 degrees, about 40 degrees, about 80 degrees, about 120 degrees, about 160 degrees, about 200 degrees, about 240 degrees, about 280 degrees, or about 320 degrees. In some embodiments, the offset between the optical axis of the imaging device and the pattern region or the illumination source on the panel may be at most about 40 degrees, about 80 degrees, about 120 degrees, about 160 degrees, about 200 degrees, about 240 degrees, about 280 degrees, about 320 degrees, or about 360 degrees.

In some embodiments, a first illumination source may be the illumination source at the shortest distance from the camera sensor. In some embodiments, the captured elevation of the first illumination source ($y_0$) may be a function of the distance of corneal reflection of the first illumination source closest to the camera ($x_0$), the angle between the normal and the corneal reflection of the first illumination source and they axis ($\theta$). In some embodiments, the angle between the normal of the corneal reflection of the first illumination source and the y-axis ($\theta$) may be a function of the distance between the first illumination source of illumination panel to the camera ($l_0$), the distance between the camera sensor and the cornea apex (d), and the distance of corneal reflection of the first illumination source closest to the camera ($x_\theta$) as shown in FIG. 4A. For example, the following mathematical relationship may provide the elevation of the first illumination:

$$y_0 = \frac{x_0}{\tan^{-1}(\theta)}$$

$$\theta = \frac{1}{2}\left[\tan^{-1}\left(\frac{l_0 - x_0}{d}\right) - \tan^{-1}\left(\frac{l_0}{d}\right)\right]$$

In some embodiments, each subsequent elevation ($y_1$, $y_2$, . . . $y_n$) of the series of illumination sources may be computed iteratively, as shown in FIG. 4B. In some embodiments, the corneal segment between ($x_{n-1}$, $y_{n-1}$) and ($x_n$, $y_n$) may be treated as an arc segment along a circle. For example, in some embodiments, the nth subsequent elevation ($y_n$) may be determined by the following mathematical relationship:

$$y_n = y_{n-1} - \frac{(x_{n-1} - x_n)(\cos t_{n-1} - \cos t_n)}{\sin t_{n-1} - \sin t_n}$$

Where $t_n$ is the angle between the tangent at ($x_n$, $y_n$) and horizontal axis In some embodiments, $t_n$ may be initially estimated to be a/2, where a is the angle between $I_n$, the nth illumination source, and the vertical axis. In some embodiments, the estimate may be refined numerically until $\Delta y_n = y_n - y_n'$ stabilizes below a preset threshold. For example, the mathematical relationship that may provide an estimate for to follows:

$$\Delta l = l_0 - l_n$$

$$\Delta y = d - y_n$$

$$a' = \cos^{-1}\frac{l_0^2 - 2\Delta y^2 - l_n^2 - \Delta l^2}{-2\sqrt{(\Delta y^2 + l_n^2)(\Delta l^2 + \Delta y^2)}}$$

$$t = \frac{\pi}{2} - \frac{a\prime}{2} - \tan^{-1}\frac{\Delta y}{\Delta l}$$

$$y_n' = y_n - \frac{x_{n-1} - x_n - (\cos t_{n-1} - \cos t)}{\sin t_{n-1} - \sin t}$$

In some embodiments, the threshold may be in the range of about 0.000001 to about 0.001. In some embodiments, the threshold may be in the range of about 0.001 to about 0.0001, about 0.001 to about 0.00001, about 0.001 to about 0.000001, about 0.0001 to about 0.00001, about 0.0001 to about 0.000001, or about 0.00001 to about 0.000001. In some embodiments, the threshold may be in the range of about 0.001, about 0.0001, about 0.00001, or about 0.000001. In some embodiments, the threshold may be in the range of at least about 0.001, about 0.0001, or about 0.00001. In some embodiments, the threshold may be in the range of at most about 0.0001, about 0.00001, or about 0.000001

III. Corneal Topography Measurement Apparatus

The systems and methods disclosed herein, in some embodiments, comprise an apparatus capable of measuring corneal topography without the need of expensive keratometry machinery or specially trained clinical personnel. Due to the ubiquitous prevalence of mobile computing devices, the present invention can harness the combination of sensors and computational power of a mobile computing device platform. For example, many mobile computing devices (smart phones) may comprise a camera, inertial sensors, onboard graphical processing unit and sufficient processing power to carry out image capture and processing with known spatial orientation. Additionally, some mobile computing devices also may have built in depth or LiDAR sensors 601 that, in some embodiments, may be utilized in combination with other sensors to measure corneal topography.

In some embodiments, the apparatus is configured to measure corneal topography by projecting light patterns 603 from a panel 605 onto a cornea. The purpose of projecting the light pattern with a known geometry onto a cornea is to measure differences in the captured reflected light pattern off of the cornea. In some embodiments, the differences in the captured reflected light pattern may be used to measure corneal curvature at a given meridian. In some embodiments, the light panel may comprise a plurality of lines coupled to the surface of the panel. In some embodiments, the lines may be linear. In some embodiments, the lines may be circular, radial, parallel, converging, diverging or any combination thereof.

In some embodiments, the lines may have a length of about 5 mm to about 30 mm. In some embodiments, the lines may have a length of about 5 mm to about 10 mm, about 5 mm to about 15 mm, about 5 mm to about 20 mm, about 5 mm to about 25 mm, about 5 mm to about 30 mm, about 10 mm to about 15 mm, about 10 mm to about 20 mm, about mm to about 25 mm, about 10 mm to about 30 mm, about 15 mm to about 20 mm, about 15 mm to about 25 mm, about 15 mm to about 30 mm, about 20 mm to about 25 mm, about 20 mm to about 30 mm, or about 25 mm to about 30 mm. In some embodiments, the lines may have a length of about 5 mm, about 10 mm, about 15 mm, about 20 mm, about 25 mm, or about 30 mm. In some embodiments, the lines may have a length of at least about 5 mm, about 10 mm, about 15 mm, about 20 mm, or about 25 mm. In some embodiments, the lines may have a length of at most about 10 mm, about 15 mm, about 20 mm, about 25 mm, or about 30 mm. In some embodiments, the lines may have a thickness of about 1 mm to about 10 mm. In some embodiments, the lines may have a thickness of about 1 mm to about 2 mm, about 1 mm to about 3 mm, about 1 mm to about 4 mm, about 1 mm to about 5 mm, about 1 mm to about 6 mm, about 1 mm to about 7 mm, about 1 mm to about 8 mm, about 1 mm to about 9 mm, about 1 mm to about 10 mm, about 2 mm to about 3 mm, about 2 mm to about 4 mm, about 2 mm to about 5 mm, about 2 mm to about 6 mm, about 2 mm to about 7 mm, about 2 mm to about 8 mm, about 2 mm to about 9 mm, about 2 mm to about 10 mm, about 3 mm to about 4 mm, about 3 mm to about 5 mm, about 3 mm to about 6 mm, about 3 mm to about 7 mm, about 3 mm to about 8 mm, about 3 mm to about 9 mm, about 3 mm to about 10 mm, about 4 mm to about 5 mm, about 4 mm to about 6 mm, about 4 mm to about 7 mm, about 4 mm to about 8 mm, about 4 mm to about 9 mm, about 4 mm to about 10 mm, about 5 mm to about 6 mm, about 5 mm to about 7 mm, about 5 mm to about 8 mm, about 5 mm to about 9 mm, about mm to about 10 mm, about 6 mm to about 7 mm, about 6 mm to about 8 mm, about 6 mm to about 9 mm, about 6 mm to about 10 mm, about 7 mm to about 8 mm, about 7 mm to about 9 mm, about 7 mm to about 10 mm, about 8 mm to about 9 mm, about 8 mm to about 10 mm, or about 9 mm to about 10 mm. In some embodiments, the lines may have a thickness of about 1 mm, about 2 mm, about 3 mm, about 4 mm, about 5 mm, about 6 mm, about 7 mm, about 8 mm, about 9 mm, or about 10 mm. In some embodiments, the lines may have a thickness of at least about 1 mm, about 2 mm, about 3 mm, about 4 mm, about 5 mm, about 6 mm, about 7 mm, about 8 mm, or about 9 mm.

In some embodiments, the lines may have a thickness of at most about 2 mm, about 3 mm, about 4 mm, about 5 mm, about 6 mm, about 7 mm, about 8 mm, about 9 mm, or about 10 mm. In some embodiments, the lines may have a thickness of about 1 mm to about 10 mm. In some embodiments, the lines may have a thickness of about 1 mm to about 2 mm, about 1 mm to about 3 mm, about 1 mm to about 4 mm, about 1 mm to about mm, about 1 mm to about 6 mm, about 1 mm to about 7 mm, about 1 mm to about 8 mm, about 1 mm to about 9 mm, about 1 mm to about 10 mm, about 2 mm to about 3 mm, about 2 mm to about 4 mm, about 2 mm to about 5 mm, about 2 mm to about 6 mm, about 2 mm to about 7 mm, about 2 mm to about 8 mm, about 2 mm to about 9 mm, about 2 mm to about 10 mm, about 3 mm to about 4 mm, about 3 mm to about 5 mm, about 3 mm to about 6 mm, about 3 mm to about 7 mm, about 3 mm to about 8 mm, about 3 mm to about 9 mm, about 3 mm to about 10 mm, about 4 mm to about 5 mm, about 4 mm to about 6 mm, about 4 mm to about 7 mm, about 4 mm to about 8 mm, about 4 mm to about 9 mm, about 4 mm to about 10 mm, about 5 mm to about 6 mm, about 5 mm to about 7 mm, about 5 mm to about 8 mm, about 5 mm to about 9 mm, about 5 mm to about 10 mm, about 6 mm to about 7 mm, about 6 mm to about 8 mm, about 6 mm to about 9 mm, about 6 mm to about 10 mm, about 7 mm to about 8 mm, about 7 mm to about 9 mm, about 7 mm to about 10 mm, about 8 mm to about 9 mm, about 8 mm to about 10 mm, or about 9 mm to about 10 mm. In some embodiments, the lines may have a thickness of about 1 mm, about 2 mm, about 3 mm, about 4 mm, about 5 mm, about 6 mm, about 7 mm, about 8 mm, about 9 mm, or about 10 mm. In some embodiments, the lines may have a thickness of at least about 1 mm, about 2 mm, about 3 mm, about 4 mm, about 5 mm, about 6 mm, about 7 mm, about 8 mm, or about 9 mm. In some embodiments, the lines may have a thickness of at most about 2 mm, about 3 mm, about 4 mm, about 5 mm, about 6 mm, about 7 mm, about 8 mm, about 9 mm, or about 10 mm.

In some embodiments, the lines may have an area of about 10 $mm^2$ to about 90 $mm^2$. In some embodiments, the lines may have an area of about 10 $mm^2$ to about 20 $mm^2$, about 10 $mm^2$ to about 30 $mm^2$, about 10 $mm^2$ to about 40 $mm^2$, about 10 $mm^2$ to about $mm^2$, about 10 mm 2 to about 60 $mm^2$, about 10 $mm^2$ to about 70 $mm^2$, about 10 $mm^2$ to about 80 $mm^2$, about 10 $mm^2$ to about 90 $mm^2$, about 20 $mm^2$ to about 30 $mm^2$, about 20 $mm^2$ to about 40 $mm^2$, about 20 $mm^2$ to about 50 $mm^2$, about 20 $mm^2$ to about 60 $mm^2$, about 20 $mm^2$ to about 70 $mm^2$, about 20 $mm^2$ to about 80 $mm^2$, about 20 $mm^2$ to about $mm^2$, about 30 $mm^2$ to about 40 $mm^2$, about 30 $mm^2$ to about 50 $mm^2$, about 30 $mm^2$ to about 60 $mm^2$, about 30 $mm^2$ to about 70 $mm^2$, about 30 $mm^2$ to about 80 $mm^2$, about 30 $mm^2$ to about 90 $mm^2$, about 40 $mm^2$ to about 50 $mm^2$, about 40 $mm^2$ to about 60 $mm^2$, about 40 $mm^2$ to about 70 $mm^2$, about 40 $mm^2$ to about 80 $mm^2$, about 40 $mm^2$ to about 90 $mm^2$, about 50 $mm^2$ to about 60 $mm^2$, about 50 $mm^2$ to about 70 $mm^2$, about 50 $mm^2$ to about 80 $mm^2$, about 50 $mm^2$ to about 90 $mm^2$, about 60 $mm^2$ to about 70 $mm^2$, about 60 $mm^2$ to about 80 $mm^2$, about 60 $mm^2$ to about 90 $mm^2$, about 70 $mm^2$ to about 80 $mm^2$, about 70 $mm^2$ to about 90 $mm^2$, or about 80 $mm^2$ to about 90 $mm^2$. In some embodiments, the lines may have an area of about 10 $mm^2$, about 20 $mm^2$, about 30 $mm^2$, about 40 $mm^2$, about 50 $mm^2$, about 60 $mm^2$, about 70 $mm^2$, about 80 $mm^2$, or about 90 $mm^2$. In some embodiments, the lines may have an area of at least about 10 $mm^2$, about 20 $mm^2$, about $mm^2$, about 40 $mm^2$, about 50 $mm^2$, about 60 $mm^2$, about 70 $mm^2$, or about 80 $mm^2$. In some embodiments, the lines may have an area of at most about 20 $mm^2$, about 30 $mm^2$, about 40 $mm^2$, about 50 $mm^2$, about 60 $mm^2$, about 70 $mm^2$, about 80 $mm^2$, or about 90 $mm^2$.

In some embodiments, the lines may have a spacing of about 1 mm to about 10 mm. In some embodiments, the lines may have a spacing of about 1 mm to about 2 mm, about 1 mm to about 3 mm, about 1 mm to about 4 mm, about 1 mm to about 5 mm, about 1 mm to about 6 mm, about 1 mm to about 7 mm, about 1 mm to about 8 mm, about 1 mm to about 9 mm, about 1 mm to about 10 mm, about 2 mm to about 3 mm, about 2 mm to about 4 mm, about 2 mm to about 5 mm, about 2 mm to about 6 mm, about 2 mm to about 7 mm, about 2 mm to about 8 mm, about 2 mm to about 9 mm, about 2 mm to about 10 mm, about 3 mm to about 4 mm, about 3 mm to about 5 mm, about 3 mm to about 6 mm, about 3 mm to about 7 mm, about 3 mm to about 8 mm, about 3 mm to about 9 mm, about 3 mm to about 10 mm, about 4 mm to about 5 mm, about 4 mm to about 6 mm, about 4 mm to about 7 mm, about 4 mm to about 8 mm, about 4 mm to about 9 mm, about 4 mm to about 10 mm, about 5 mm to about 6 mm, about 5 mm to about 7 mm, about 5 mm to about 8 mm, about 5 mm to about 9 mm, about 5 mm to about 10 mm, about 6 mm to about 7 mm, about 6 mm to about 8 mm, about 6 mm to about 9 mm, about 6 mm to about mm, about 7 mm to about 8 mm, about 7 mm to about 9 mm, about 7 mm to about 10 mm, about 8 mm to about 9 mm, about 8 mm to about 10 mm, or about 9 mm to about 10 mm. In some embodiments, the lines may have a spacing of about 1 mm, about 2 mm, about 3 mm, about 4 mm, about 5 mm, about 6 mm, about 7 mm, about 8 mm, about 9 mm, or about 10 mm. In some embodiments, the lines may have a spacing of at least about 1 mm, about 2 mm, about 3 mm, about 4 mm, about 5 mm, about 6 mm, about 7 mm, about 8 mm, or about 9 mm. In some embodiments, the lines may have a spacing of at most about 2 mm, about 3 mm, about 4 mm, about 5 mm, about 6 mm, about 7 mm, about 8 mm, about 9 mm, or about 10 mm.

Figure 6A:
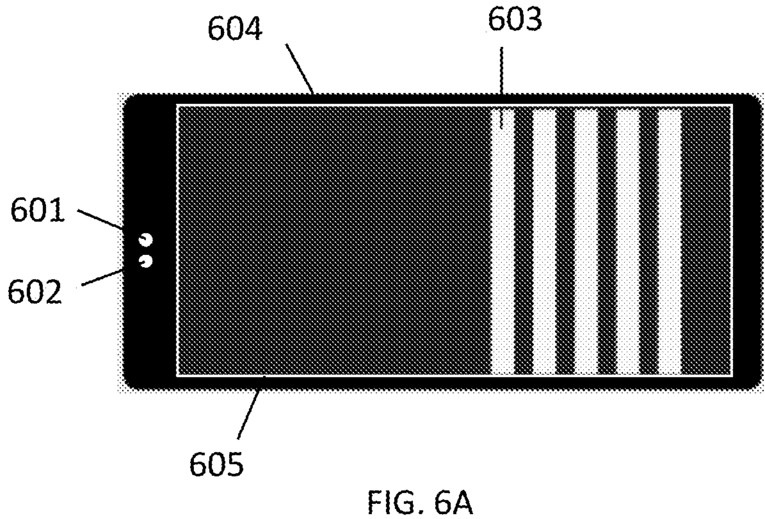
FIGS. 6A-6B illustrate the position and geometry of a light illumination pattern on a mobile device utilizing the mobile device screen to project the light illumination pattern. Two configurations in both portrait and landscape orientations are shown, in accordance with some embodiments.
Figure 6B:
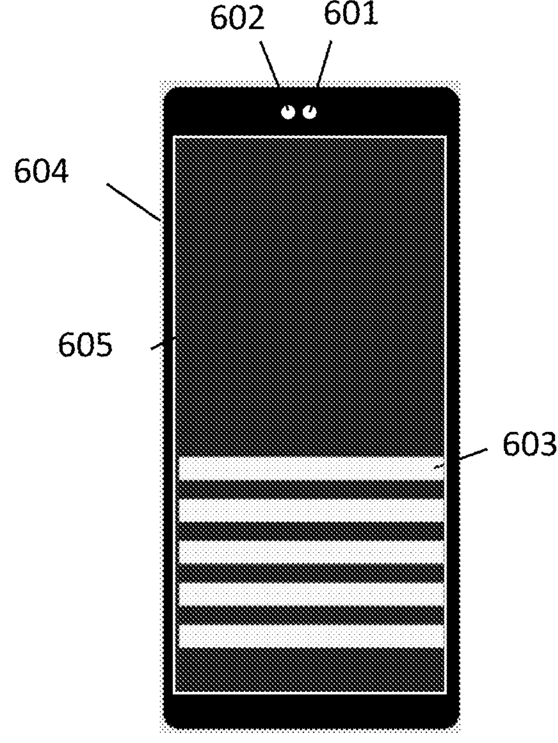

In some embodiments, the apparatus may comprise a light panel 605 that is integrated with the mobile computing device 604, as seen in FIG. 6A-6B. In some embodiments, the integrated light panel 605 may comprise a light pattern 603 where the first light pattern source is at a distance from the camera sensor of the mobile computing device 602. In some embodiments the distance between the first light pattern source may be about 1 mm to about 10 mm. In some embodiments the distance between the first light pattern source may be about 1 mm to about 2 mm, about 1 mm to about 3 mm, about 1 mm to about 4 mm, about 1 mm to about 5 mm, about 1 mm to about 6 mm, about 1 mm to about 7 mm, about 1 mm to about 8 mm, about 1 mm to about 9 mm, about 1 mm to about 10 mm, about 2 mm to about 3 mm, about 2 mm to about 4 mm, about 2 mm to about 5 mm, about 2 mm to about 6 mm, about 2 mm to about 7 mm, about 2 mm to about 8 mm, about 2 mm to about 9 mm, about 2 mm to about 10 mm, about 3 mm to about 4 mm, about 3 mm to about 5 mm, about 3 mm to about 6 mm, about 3 mm to about 7 mm, about 3 mm to about 8 mm, about 3 mm to about 9 mm, about 3 mm to about 10 mm, about 4 mm to about 5 mm, about 4 mm to about 6 mm, about 4 mm to about 7 mm, about 4 mm to about 8 mm, about 4 mm to about 9 mm, about 4 mm to about 10 mm, about 5 mm to about 6 mm, about 5 mm to about 7 mm, about 5 mm to about 8 mm, about 5 mm to about 9 mm, about 5 mm to about 10 mm, about 6 mm to about 7 mm, about 6 mm to about 8 mm, about 6 mm to about 9 mm, about 6 mm to about 10 mm, about 7 mm to about 8 mm, about 7 mm to about 9 mm, about 7 mm to about 10 mm, about 8 mm to about 9 mm, about 8 mm to about 10 mm, or about 9 mm to about 10 mm. In some embodiments the distance between the first light pattern source may be about 1 mm, about 2 mm, about 3 mm, about 4 mm, about 5 mm, about 6 mm, about 7 mm, about 8 mm, about 9 mm, or about 10 mm. In some embodiments the distance between the first light pattern source may be at least about 1 mm, about 2 mm, about 3 mm, about 4 mm, about 5 mm, about 6 mm, about 7 mm, about 8 mm, or about 9 mm. In some embodiments the distance between the first light pattern source may be at most about 2 mm, about 3 mm, about 4 mm, about 5 mm, about 6 mm, about 7 mm, about 8 mm, about 9 mm, or about 10 mm.

Figure 7A:
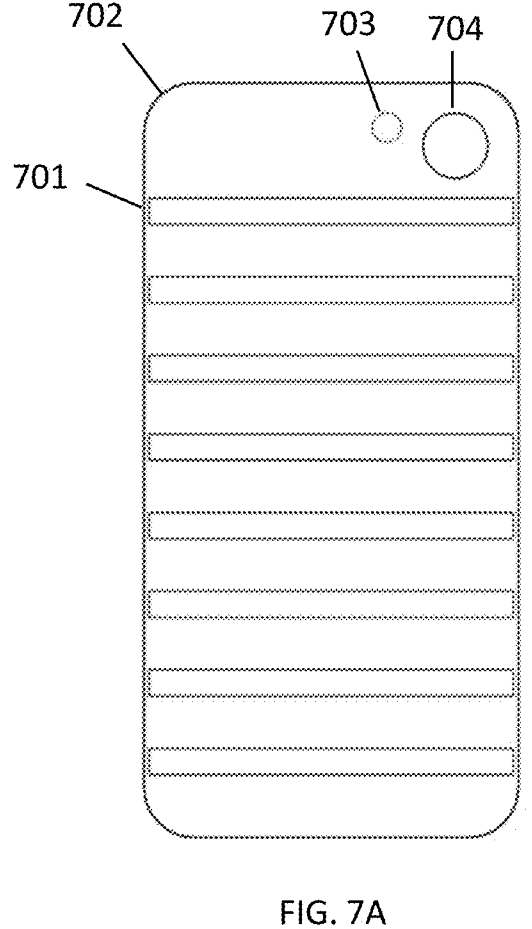
FIGS. 7A-7B illustrate a passive linear and circular light pattern panel that may be releasably coupled to a mobile device, in accordance with some embodiments.
Figure 7B:
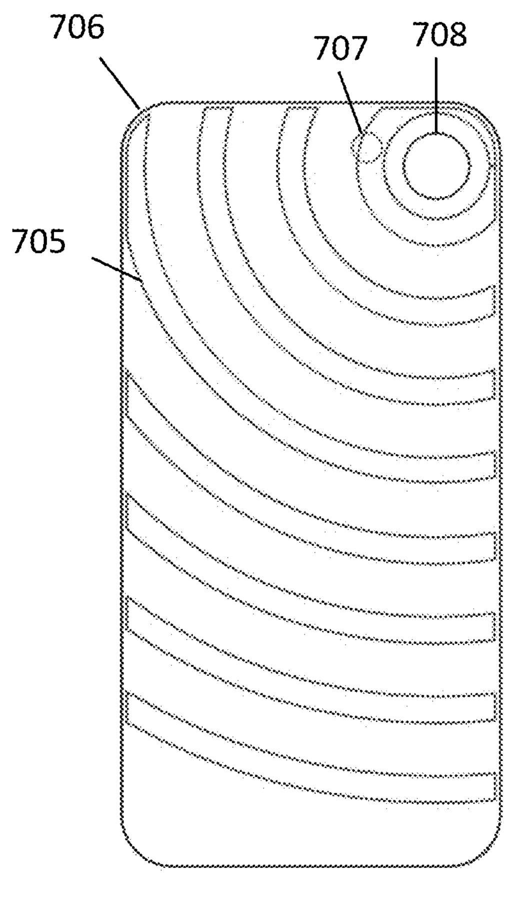

In some embodiments, the panel may be releasably coupled to a mobile computing device as seen in FIG. 7A-7B. In some embodiments, the panel 702 and 706 may be releasably coupled to a mobile computing device by a quick release mechanism that enables rapid attachment and removal of the panel from the mobile device. In some embodiments, the quick release mechanism may comprise a snap-fit, lip and groove, hook and clasp mechanism or any combination thereof. In some embodiments, the panel may serve as a protective case for the mobile computing device. In some embodiments, the panel may comprise a plurality of lines. In some embodiments, the plurality of lines may be linear 701. In some embodiments, the plurality of lines may be circular or radial 705. In some embodiments, the panel may have cut outs for the camera sensor 704 and 708 and built-in illumination source 703 and 707. In some embodiments, the panel 702 and 706, may be transparent or translucent. In some embodiments, the panel may be comprised of polymethyl methacrylate (PMMA). In some embodiments, the panel may be opaque, transparent, or semi-transparent. Alternatively, the panel may be comprised of transparent or opaque segments. In some embodiments, the transparent or opaque segments may act as a wave guide to create an illuminated pattern. In some embodiments, the panel may have a thickness of about 0.3 mm to about 3 mm. In some embodiments, the panel may have a thickness of about 0.3 mm to about 0.6 mm, about 0.3 mm to about 0.9 mm, about 0.3 mm to about 2.1 mm, about 0.3 mm to about 2.4 mm, about 0.3 mm to about 2.7 mm, about 0.3 mm to about 3 mm, about 0.6 mm to about 0.9 mm, about 0.6 mm to about 2.1 mm, about 0.6 mm to about 2.4 mm, about 0.6 mm to about 2.7 mm, about 0.6 mm to about 3 mm, about 0.9 mm to about 2.1 mm, about 0.9 mm to about 2.4 mm, about 0.9 mm to about 2.7 mm, about 0.9 mm to about 3 mm, about 2.1 mm to about 2.4 mm, about 2.1 mm to about 2.7 mm, about 2.1 mm to about 3 mm, about 2.4 mm to about 2.7 mm, about 2.4 mm to about 3 mm, or about 2.7 mm to about 3 mm. In some embodiments, the panel may have a thickness of about 0.3 mm, about 0.6 mm, about 0.9 mm, about 2.1 mm, about 2.4 mm, about 2.7 mm, or about 3 mm. In some embodiments, the panel may have a thickness of at least about 0.3 mm, about 0.6 mm, about 0.9 mm, about 2.1 mm, about 2.4 mm, or about 2.7 mm. In some embodiments, the panel may have a thickness of at most about 0.6 mm, about 0.9 mm, about 2.1 mm, about 2.4 mm, about 2.7 mm, or about 3 mm.

In some embodiments, the panel may comprise segments of material with high scattering coefficient. In some embodiments, the segments of the panel of high scattering coefficient may create an illumination pattern. In some embodiments, the panel may have a refractive index of about 1.3 to about 1.5. In some embodiments, the panel may have a refractive index of about 1.3 to about 1.32, about 1.3 to about 1.34, about 1.3 to about 1.36, about 1.3 to about 1.38, about 1.3 to about 1.4, about 1.3 to about 1.42, about 1.3 to about 1.44, about 1.3 to about 1.46, about 1.3 to about 1.48, about 1.3 to about 1.5, about 1.32 to about 1.34, about 1.32 to about 1.36, about 1.32 to about 1.38, about 1.32 to about 1.4, about 1.32 to about 1.42, about 1.32 to about 1.44, about 1.32 to about 1.46, about 1.32 to about 1.48, about 1.32 to about 1.5, about 1.34 to about 1.36, about 1.34 to about 1.38, about 1.34 to about 1.4, about 1.34 to about 1.42, about 1.34 to about 1.44, about 1.34 to about 1.46, about 1.34 to about 1.48, about 1.34 to about 1.5, about 1.36 to about 1.38, about 1.36 to about 1.4, about 1.36 to about 1.42, about 1.36 to about 1.44, about 1.36 to about 1.46, about 1.36 to about 1.48, about 1.36 to about 1.5, about 1.38 to about 1.4, about 1.38 to about 1.42, about 1.38 to about 1.44, about 1.38 to about 1.46, about 1.38 to about 1.48, about 1.38 to about 1.5, about 1.4 to about 1.42, about 1.4 to about 1.44, about 1.4 to about 1.46, about 1.4 to about 1.48, about 1.4 to about 1.5, about 1.42 to about 1.44, about 1.42 to about 1.46, about 1.42 to about 1.48, about 1.42 to about 1.5, about 1.44 to about 1.46, about 1.44 to about 1.48, about 1.44 to about 1.5, about 1.46 to about 1.48, about 1.46 to about 1.5, or about 1.48 to about 1.5. In some embodiments, the panel may have a refractive index of about 1.3, about 1.32, about 1.34, about 1.36, about 1.38, about 1.4, about 1.42, about 1.44, about 1.46, about 1.48, or about 1.5. In some embodiments, the panel may have a refractive index of at least about 1.3, about 1.32, about 1.34, about 1.36, about 1.38, about 1.4, about 1.42, about 1.44, about 1.46, or about 1.48. In some embodiments, the panel may have a refractive index of at most about 1.32, about 1.34, about 1.36, about 1.38, about 1.4, about 1.42, about 1.44, about 1.46, about 1.48, or about 1.5.

In some embodiments, the panel may have an absorption coefficient of about 1 cm^−1 to about 10 cm^−1. In some embodiments, the panel may have an absorption coefficient of about 1 cm^−1 to about 2 cm^−1, about 1 cm^−1 to about 3 cm^−1, about 1 cm^−1 to about 4 cm^−1, about 1 cm^−1 to about 5 cm^−1, about 1 cm^−1 to about 6 cm^−1, about 1 cm^−1 to about 7 cm^−1, about 1 cm^−1 to about 8 cm^−1, about 1 cm^−1 to about 9 cm^−1, about 1 cm^−1 to about 10 cm^−1, about 2 cm^−1 to about 3 cm^−1, about 2 cm^−1 to about 4 cm^−1, about 2 cm^−1 to about 5 cm^−1, about 2 cm^−1 to about 6 cm^−1, about 2 cm^−1 to about 7 cm^−1, about 2 cm^−1 to about 8 cm^−1, about 2 cm^−1 to about 9 cm^−1, about 2 cm^−1 to about 10 cm^−1, about 3 cm^−1 to about 4 cm^−1, about 3 cm^−1 to about 5 cm^−1, about 3 cm^−1 to about 6 cm^−1, about 3 cm^−1 to about 7 cm^−1, about 3 cm^−1 to about 8 cm^−1, about 3 cm^−1 to about 9 cm^−1, about 3 cm^−1 to about 10 cm^−1, about 4 cm^−1 to about 5 cm^−1, about 4 cm^−1 to about 6 cm^−1, about 4 cm^−1 to about 7 cm^−1, about 4 cm^−1 to about 8 cm^−1, about 4 cm^−1 to about 9 cm^−1, about 4 cm^−1 to about cm^−1, about 5 cm^−1 to about 6 cm^−1, about 5 cm^−1 to about 7 cm^−1, about 5 cm^-1 to about 8 cm^−1, about 5 cm^−1 to about 9 cm^−1, about 5 cm^−1 to about 10 cm^−1, about 6 cm^−1 to about 7 cm^−1, about 6 cm^−1 to about 8 cm^−1, about 6 cm^−1 to about 9 cm^−1, about 6 cm^−1 to about 10 cm^−1, about 7 cm^−1 to about 8 cm^−1, about 7 cm^-1 to about 9 cm^−1, about 7 cm^−1 to about 10 cm^−1, about 8 cm^−1 to about 9 cm^−1, about 8 cm^−1 to about 10 cm^−1, or about 9 cm^−1 to about 10 cm^−1. In some embodiments, the panel may have an absorption coefficient of about 1 cm^−1, about 2 cm^−1, about 3 cm^−1, about 4 cm^−1, about 5 cm^−1, about 6 cm^−1, about 7 cm^−1, about 8 cm^−1, about 9 cm^−1, or about 10 cm^−1. In some embodiments, the panel may have an absorption coefficient of at least about 1 cm^−1, about 2 cm^−1, about 3 cm^−1, about 4 cm^−1, about 5 cm^−1, about 6 cm^−1, about 7 cm^−1, about 8 cm^−1, or about 9 cm^−1. In some embodiments, the panel may have an absorption coefficient of at most about 2 cm^−1, about 3 cm^−1, about 4 cm^−1, about 5 cm^−1, about 6 cm^−1, about 7 cm^−1, about 8 cm^−1, about 9 cm^−1, or about 10 cm^−1.

In some embodiments, the panel lines may be opaque. In some embodiments, the panel may comprise a waveguide that harness the integrated illumination source of the mobile computing device. In some embodiments, the waveguide may comprise a lens-based system to couple the light from the integrated illumination source to the waveguide without losing light to total internal reflection between the interface of the illumination source and the waveguide. In some embodiments, up to 10%, up to 20%, up to 30%, up to 40% up to 50%, up to 60%, up to 70% up to 80%, up to 90% or up to 100% of the output light from the integrated illumination source is coupled into the waveguide. In some embodiments, the lens-based system may comprise a ball lens, fish eye lens, wide angle lens, macro lens, normal lens, or telephoto lens. In some embodiments, the panel may comprise an integrated camera sensor lens system that provides an optical power than what is achievable by the mobile computing device camera sensor alone. In some embodiments, the optical power may be about 5 diopters to about 40 diopters. In some embodiments, the optical power may be about 5 diopters to about 10 diopters, about 5 diopters to about 15 diopters, about 5 diopters to about 20 diopters, about 5 diopters to about 25 diopters, about 5 diopters to about 30 diopters, about 5 diopters to about 35 diopters, about 5 diopters to about 40 diopters, about 10 diopters to about 15 diopters, about 10 diopters to about 20 diopters, about 10 diopters to about 25 diopters, about 10 diopters to about 30 diopters, about 10 diopters to about 35 diopters, about 10 diopters to about 40 diopters, about 15 diopters to about 20 diopters, about 15 diopters to about 25 diopters, about 15 diopters to about 30 diopters, about 15 diopters to about 35 diopters, about 15 diopters to about 40 diopters, about 20 diopters to about 25 diopters, about 20 diopters to about 30 diopters, about 20 diopters to about 35 diopters, about 20 diopters to about 40 diopters, about 25 diopters to about 30 diopters, about 25 diopters to about 35 diopters, about 25 diopters to about 40 diopters, about 30 diopters to about 35 diopters, about 30 diopters to about 40 diopters, or about 35 diopters to about 40 diopters. In some embodiments, the optical power may be about 5 diopters, about 10 diopters, about 15 diopters, about 20 diopters, about 25 diopters, about 30 diopters, about 35 diopters, or about 40 diopters. In some embodiments, the optical power may be at least about 5 diopters, about 10 diopters, about 15 diopters, about 20 diopters, about 25 diopters, about diopters, or about 35 diopters. In some embodiments, the optical power may be at most about 10 diopters, about 15 diopters, about 20 diopters, about 25 diopters, about 30 diopters, about 35 diopters, or about 40 diopters.

Figure 8A:
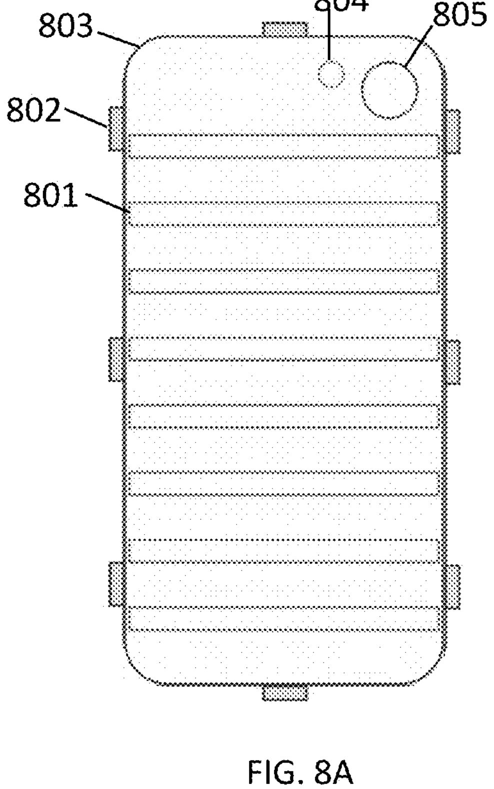
FIGS. 8A-8B illustrate an active linear and circular light pattern panel with an integrated seed illumination source that may be releasably coupled to a mobile device, in accordance with some embodiments.
Figure 8B:
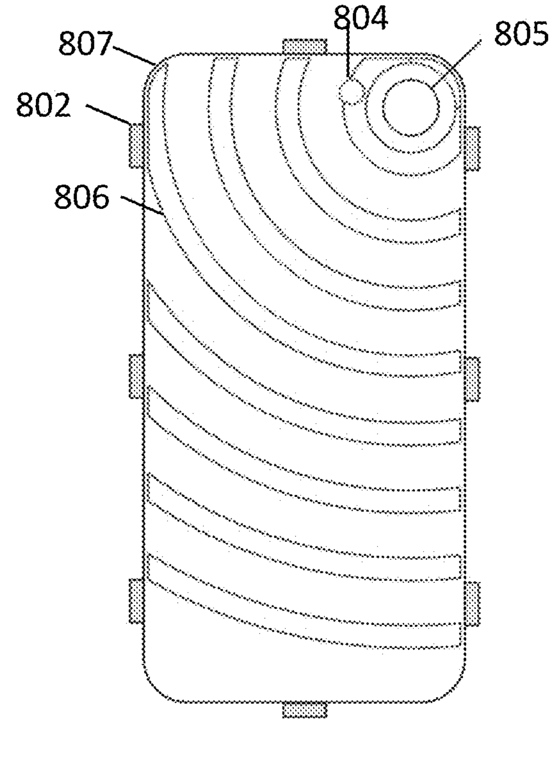

In some embodiments, the panel 803 and 807 may comprise an illumination source 802, as seen in FIG. 8A-8B. In some embodiments the illumination source may comprise a light emitting diode (LED), super luminescent diode (SLD), low coherent laser, highly coherent laser, wide band laser, narrow band laser, halogen bulb, xenon lam or any combination thereof. In some embodiments, the illumination source may comprise a battery to power the illumination source. In some embodiments, the mobile computing device can be configured to power the illumination source. In some embodiments, the illumination may be independently controlled by a physical on-off switch. In some embodiments, the illumination source may be in electrical communication with the mobile computing device to digitally control the emission. In some embodiments, the mobile device may provide a variable illumination signal to tune the brightness of the illumination source. In some embodiments, the panel comprising an illumination source may comprise a plurality of illumination lines. In some embodiments, the plurality of illumination lines may be linear 801. In some embodiments, the plurality of illumination lines may be circular or radial 806. In some embodiments, the panel 803 and 807 comprising an illumination source may further comprise cut outs for the mobile device camera sensor 805 and integrated illumination source 804.

Figure 10:
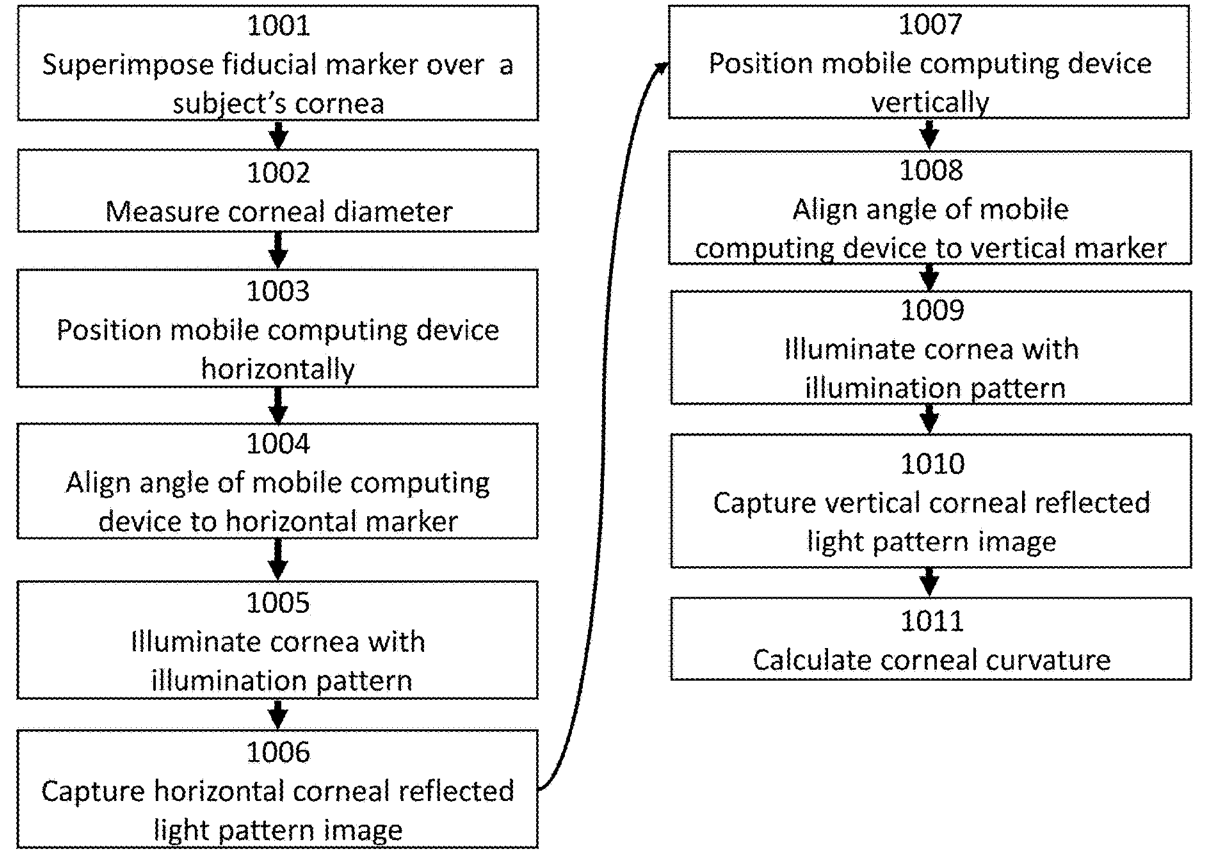
FIG. 10 shows a workflow of measuring corneal topography of a given subject's cornea.

The methods disclosed herein, in some embodiments, comprise a method for using the corneal topography measurement apparatus to measure a subject's corneal diameter and topography, as can be seen in FIG. 10, comprising: (a) superimposing a fiducial marker over a subject's cornea 1001; (b) measuring a subject's corneal diameter 1002; (c) positioning a mobile computing device horizontally 1003; (d) aligning an angle of the mobile computing device to a horizontal marker 1004; (e) illuminating the subject's cornea with an illumination pattern 1005; (f) capturing a horizontal image of the corneal reflected light pattern 1006; (g) positioning the mobile computing device vertically 1007; (h) aligning the angle of the mobile computing device to a vertical marker 1008; (i) illuminating the subject's cornea with an illumination pattern 1009; (j) capturing a vertical image of the corneal reflected light pattern 1010 and (k) calculating the subject's corneal curvature and topography 1011. In some embodiments, a plurality of positions between vertical and horizontal positions of the mobile computing device may be utilized to acquire densely sampled corneal topographical data. In some embodiments, a continual video of a corneal reflected light pattern may be acquired in place of discrete images at the horizontal and vertical positions.

IV. Graphical User Interface Kits

In some embodiments, the apparatus for corneal topographical measurement may comprise a mobile device application with a graphical user interface (GUI) kit to guide the subject or operator to appropriately measure corneal topography, as shown in FIGS. 9A-9C, 11A-11D, 12A-12F and 13A-13E. In some embodiments, the graphical user interface may comprise large buttons 903 and text box descriptions 902 of the task or actions the user or operator must complete, as seen in FIGS. 9A and 11A-11D. In some embodiments, the GUI may comprise an augmented reality (AR) overlay of a shape 901 or shapes 904 and 905 to guide the user during the particular action to complete the task at hand as seen in FIG. 9B. In some embodiments, the GUI AR overlay may comprise one or more concentric circles 901 to position a mobile computing device camera sensor over a subject's cornea, align the angular orientation of the camera sensor with respect to either vertical or horizontal axis of the cornea or any combination thereof.

In some embodiments, the circle GUI AR overlay element may be used to determine the diameter of the subject's cornea. In some embodiments, the GUI AR overlay elements may dynamically move or adjust in size and orientation upon movement of the mobile computing device. In some embodiments, two concentric GUI AR overlay elements 904 and 905 may be utilized to align and guide the orientation of the mobile computing device with respect to the patient's cornea, as can be seen in FIG. 9B-9C. In some embodiments, the GUI may comprise an indicator text box 906 to highlight what step the user or operator is currently completing and how many steps remain till the completion of all corneal measurements. In some embodiments, GUI elements and AR overlays may be used to measure corneal diameter FIGS. 11A-11D, portrait (vertical) corneal topography FIGS. 13A-13E and landscape (horizontal) corneal topography FIGS. 12A-12F.

Figures 11A, 11B, 11C, 11D:
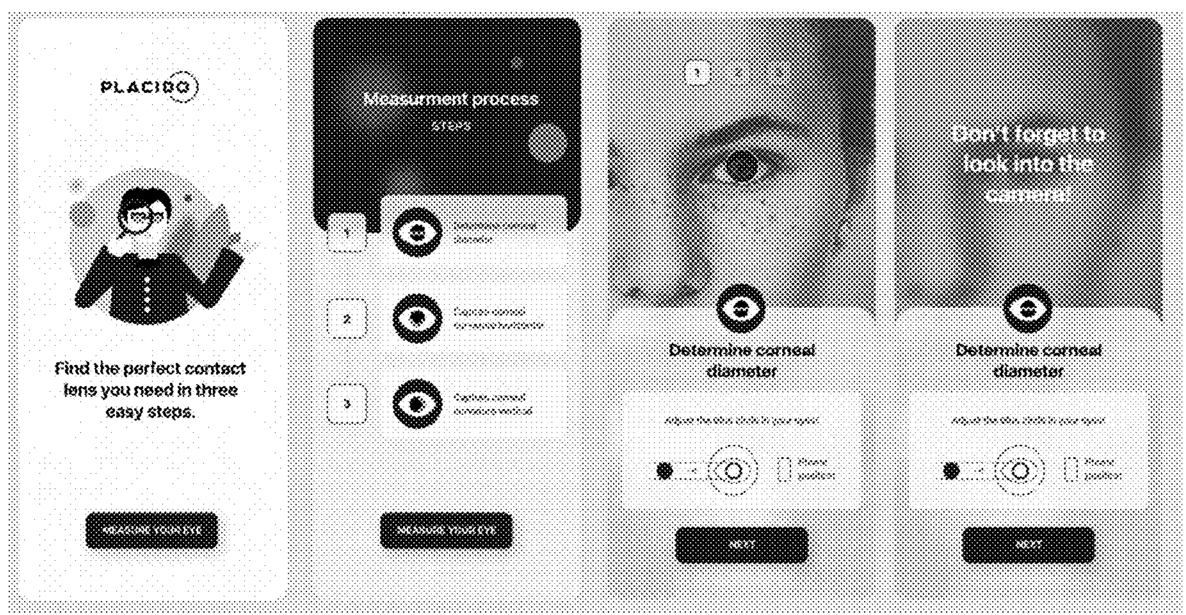
FIGS. 11A-11D illustrates the user-friendly and intuitive graphical user interface that guides a subject step-by-step to measure the subject's corneal diameter, in accordance with some embodiments.

In some embodiments, the GUI elements and AR overlay may be configured to assist a user in measuring corneal diameter, as can be seen in FIG. 11. In some embodiments, the user may be presented with a GUI view of a home screen comprising a graphic, company name, logo, instructional text, a large button or any combination thereof as seen in FIG. 11A. In some embodiments, the instructional text may comprise instructions on the goal of the following GUI views to follow. In some embodiments, the large button may comprise text indicating the function of tapping or pressing the button. In some embodiments, the text may read "measure your eye". In some embodiments, upon pressing or tapping the button in GUI view shown in FIG. 11A, the user may be shown a GUI view of FIG. 11B. In some embodiments, the GUI view of FIG. 11B may comprise a plurality of text boxes comprising instructional text, header information text, a large button or any combination thereof. In some embodiments, the plurality of text boxes may comprise text indicating the steps of the procedures for measuring a subject's corneal topography. In some embodiments, the text may comprise the steps of: (1) determining corneal diameter, (2) capturing corneal horizontal curvature and (3) capturing corneal vertical curvature. In some embodiments, the text may comprise the steps of: (1) determining the corneal diameter, and (2) capturing a plurality of corneal curvature measurements at a plurality of meridians. In some embodiments, each meridian may comprise a different set of angular polar coordinates. In some embodiments, the polar coordinates may comprise a fixed radial coordinate with a varying angular coordinate.

In some embodiments, the angular coordinate may comprise about 0 degrees to about 360 degrees. In some embodiments, the angular coordinate may comprise about 0 degrees to about 40 degrees, about 0 degrees to about 80 degrees, about 0 degrees to about 120 degrees, about 0 degrees to about 160 degrees, about 0 degrees to about 200 degrees, about 0 degrees to about 240 degrees, about 0 degrees to about 280 degrees, about 0 degrees to about 320 degrees, about 0 degrees to about 360 degrees, about 40 degrees to about 80 degrees, about 40 degrees to about 120 degrees, about 40 degrees to about 160 degrees, about 40 degrees to about 200 degrees, about 40 degrees to about 240 degrees, about 40 degrees to about 280 degrees, about 40 degrees to about 320 degrees, about 40 degrees to about 360 degrees, about 80 degrees to about 120 degrees, about 80 degrees to about 160 degrees, about 80 degrees to about 200 degrees, about 80 degrees to about 240 degrees, about 80 degrees to about 280 degrees, about 80 degrees to about 320 degrees, about 80 degrees to about 360 degrees, about 120 degrees to about 160 degrees, about 120 degrees to about 200 degrees, about 120 degrees to about 240 degrees, about 120 degrees to about 280 degrees, about 120 degrees to about 320 degrees, about 120 degrees to about 360 degrees, about 160 degrees to about 200 degrees, about 160 degrees to about 240 degrees, about 160 degrees to about 280 degrees, about 160 degrees to about 320 degrees, about 160 degrees to about 360 degrees, about 200 degrees to about 240 degrees, about 200 degrees to about 280 degrees, about 200 degrees to about 320 degrees, about 200 degrees to about 360 degrees, about 240 degrees to about 280 degrees, about 240 degrees to about 320 degrees, about 240 degrees to about 360 degrees, about 280 degrees to about 320 degrees, about 280 degrees to about 360 degrees, or about 320 degrees to about 360 degrees. In some embodiments, the angular coordinate may comprise about 0 degrees, about 40 degrees, about 80 degrees, about 120 degrees, about 160 degrees, about 200 degrees, about 240 degrees, about 280 degrees, about 320 degrees, or about 360 degrees.

In some embodiments, the angular coordinate may comprise at least about 0 degrees, about 40 degrees, about 80 degrees, about 120 degrees, about 160 degrees, about 200 degrees, about 240 degrees, about 280 degrees, or about 320 degrees. In some embodiments, the angular coordinate may comprise at most about 40 degrees, about 80 degrees, about 120 degrees, about 160 degrees, about 200 degrees, about 240 degrees, about 280 degrees, about 320 degrees, or about 360 degrees.

In some embodiments, the plurality of meridians may comprise about 8 meridians to about 365 meridians. In some embodiments, the plurality of meridians may comprise about 8 meridians to about 16 meridians, about 8 meridians to about 32 meridians, about 8 meridians to about 64 meridians, about 8 meridians to about 128 meridians, about 8 meridians to about 256 meridians, about 8 meridians to about 365 meridians, about 16 meridians to about 32 meridians, about 16 meridians to about 64 meridians, about 16 meridians to about 128 meridians, about 16 meridians to about 256 meridians, about 16 meridians to about 365 meridians, about 32 meridians to about 64 meridians, about 32 meridians to about 128 meridians, about 32 meridians to about 256 meridians, about 32 meridians to about 365 meridians, about 64 meridians to about 128 meridians, about 64 meridians to about 256 meridians, about 64 meridians to about 365 meridians, about 128 meridians to about 256 meridians, about 128 meridians to about 365 meridians, or about 256 meridians to about 365 meridians. In some embodiments, the plurality of meridians may comprise about 8 meridians, about 16 meridians, about 32 meridians, about 64 meridians, about 128 meridians, about 256 meridians, or about 365 meridians. In some embodiments, the plurality of meridians may comprise at least about 8 meridians, about 16 meridians, about 32 meridians, about 64 meridians, about 128 meridians, or about 256 meridians. In some embodiments, the plurality of meridians may comprise at most about 16 meridians, about 32 meridians, about 64 meridians, about 128 meridians, about 256 meridians, or about 365 meridians.

In some embodiments, each text box may be placed adjacent to a numeral indicating the order of steps to be performed. In some embodiments, the text box comprising text indicators of each step may further comprise a graphic indicating the step in graphical form adjacent to the text indicator as can be seen in FIG. 11B. Once the user presses or taps the button shown in FIG. 11B, the user may be shown the GUI view in FIG. 11C. In some embodiments, the user may be shown a GUI view comprising a transparent AR circle overlay, a real-time image of the subject's cornea and eye in the field of view of the camera, a plurality of alpha numeric text and graphical indicators, a large button or any combination thereof as seen in FIG. 11C. In some embodiments, the plurality of alpha numeric text and graphical indicators may comprise a series of Arabic numerals within a defined text graphic that may indicate the total number of steps for measuring a subject's corneal topography. In some embodiments, the numeral of the current procedural step of measuring a subject's corneal topography may be highlighted to indicate the present step. In some embodiments, the remaining numeral indicators may be transparent to indicate that the user is not completing the particular step. In some embodiments, the plurality of alpha numeric text and graphical indicators may comprise instructional text and a graphic instructing the user on how to measure a subject's corneal diameter. In some embodiments, the text may comprise the directions of adjusting the AR projected circle overlay in the subject's eyes. In some embodiments, the text may be adjacent to a graphical representation of the instructions of the text. In some embodiments, the user may move the camera in space to appropriately align the AR projected circle to fully encompass the subject's eye as shown in FIG. 11C. In some embodiments, the user may progress to the next step or GUI view by pressing or tapping the large button with a title of "next". In some embodiments, the user may then be shown a GUI view comprising a plurality of text and graphical instructions, a blurred real-time image of the subject's cornea and eye in the field of view of the camera, a large button or any combination thereof, as can be seen in FIG. 11D. In some embodiments, the plurality of alpha numeric text and graphical indicators may comprise instructional text and a graphic instructing the user on how to measure a subject's corneal diameter. In some embodiments, the text may comprise the directions of adjusting the AR projected circle overlay in the subject's eyes.

In some embodiments, the text may be adjacent to a graphical representation of the instructions of the text. In some embodiments, the instructional text superimposed upon the blurred real-time image of the subject's cornea and eye in the field of the camera may indicate to the user to look into the camera to insure proper image acquisition. In some embodiments, the user may then advance to the next GUI view by pressing or tapping the large button titled "next".

Figures 12A, 12B, 12C, 12D, 12E, 12F:
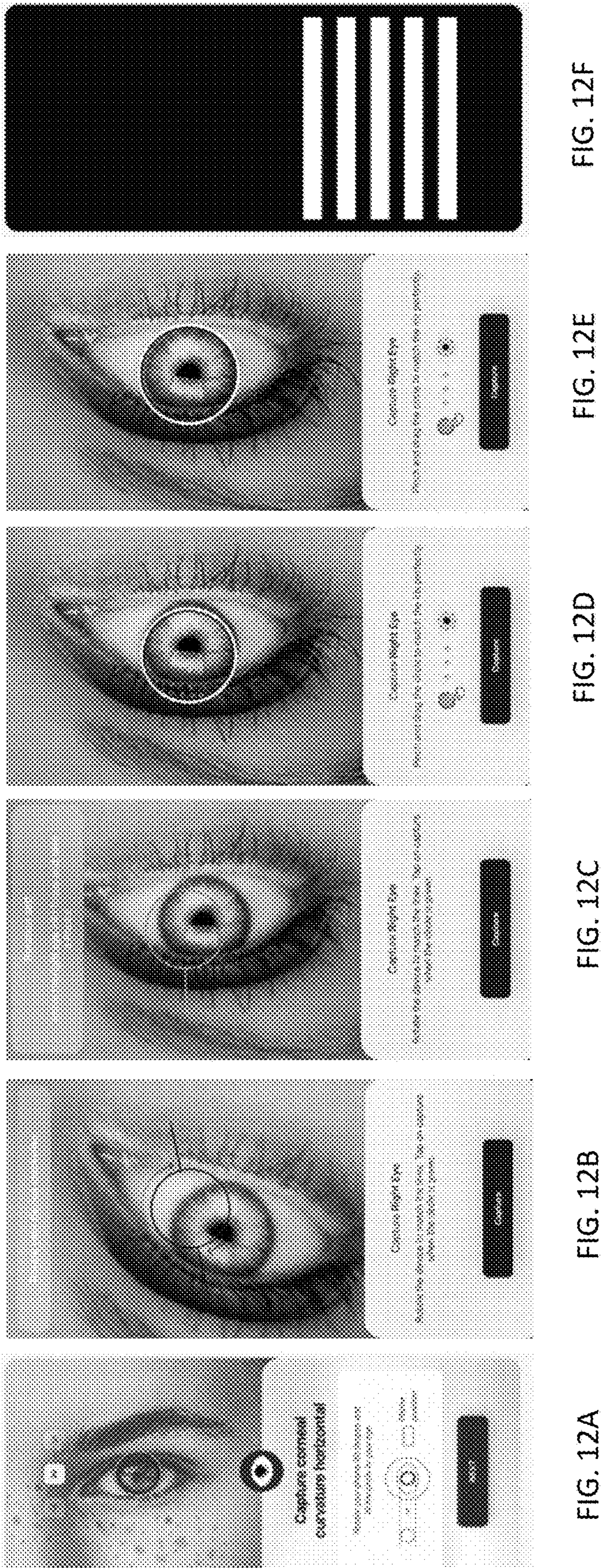
FIGS. 12A-12F illustrate the user-friendly and intuitive graphical user interface that guides a subject step-by-step to measure corneal topography in a horizontal orientation, in accordance with some embodiments.

In some embodiments, the GUI elements and AR overlay may be configured to assist a user in acquiring corneal topography in a horizontal orientation of a mobile device, as seen in FIGS. 12A-12F. Beginning with FIG. 12A, a user may be instructed by a pop-up text window on how to orient the mobile phone with respect to the cornea indicating that the user will be acquiring data for a horizontal aspect of the corneal curvature. In some embodiments, the view of FIG. 12A may comprise a circular AR overlay that may be used by the user to position the distance and macroscopic alignment of the mobile device and camera sensor with respect to a displayed real-time image of the subject's eye and cornea. In some embodiments, sufficient alignment may occur when the circular AR overlay encompasses the cornea in its entirety, as shown in FIG. 12A. In some embodiments, the GUI view of FIG. 12A may also indicate to the user visually at the top of the view in a highlighted text window comprising a numeral of the step or portion of the total steps that is being conducted. In some embodiments, the user may then advance to acquiring data by tapping a large button with the indicator of "next". In some embodiments, the user may be shown the view, as can be seen in FIG. 12B, where the GUI comprises a set of text instructions and a circular GUI AR overlay element presented on a background of the image of what is in the field of view of the camera at the time the user has advanced to the view of FIG. 12B. In some embodiments, the circular GUI AR overlay element may comprise two-line elements separated by 180 degrees connected to the circular GUI AR overlay element in addition to a dotted line element traversing the vertical axis of the user's eye. In some embodiments, the two-line elements separated by 180 degrees connected to the circular GUI AR overlay element may be aligned with the dotted line element traversing the vertical length of the user's eye to properly align the mobile computing device to measure corneal curvature in the horizontal plane. In some embodiments, the text instructions of FIG. 12B may inform the user that the user may need to rotate the body of the mobile computing device to align the camera sensor of the mobile computing device and the orientation of the horizontal axis of the subject's cornea. In some embodiments, upon rotating the mobile computing device to align the circular GUI AR elements shown in FIG. 12B, the user may then be presented with a view as seen in FIG. 12C. In some embodiments, the user may be presented with a circular GUI AR overlay element that may comprise two-line elements separated by 180 degrees connected to the circular GUI AR overlay element that is a different color than the circular GUI overlay element of FIG. 12B. In some embodiments, the circular GUI AR overlay element of a different color may be presented on a background of the image of what is in the field of view of the camera at the time the user has advanced to the view of FIG. 12C. In some embodiments, the user may also be presented with text notifying the user that the rotation of the mobile computing device has been properly set and that the user may proceed to capture a corneal curvature measurement. In some embodiments, the user may then be presented to view of FIG. 12D comprising a set of concentric colored circle GUI AR elements and text instructions. In some embodiments, the text instructions may describe to the user with a combination of text and graphics how to move the set of concentric colored circular GUI AR elements to superimpose the concentric colored circular GUI AR elements on the user's iris as seen in FIG. 12E. In some embodiments, the user may then capture a corneal curvature measurement by tapping or pressing the capture button presented within the text field seen in FIG. 12E. In some embodiments, the user may then be presented with an illumination pattern seen in FIG. 12F.

Figures 13A, 13B, 13C, 13D, 13E:
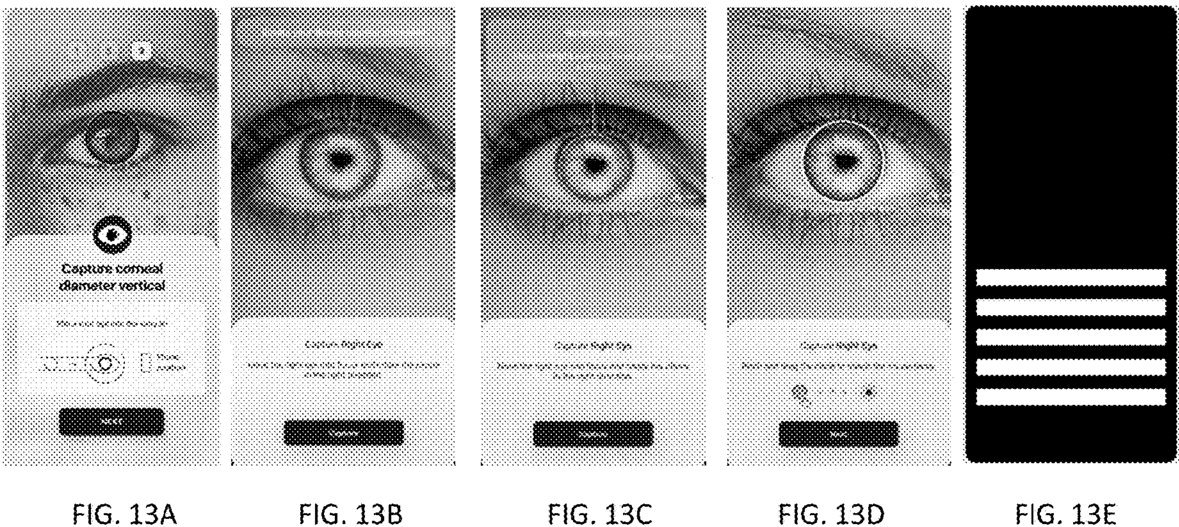
FIGS. 13A-13E illustrate the user-friendly and intuitive graphical user interface that guides a subject step-by-step to measure corneal topography in a vertical orientation, in accordance with some embodiments.

In some embodiments, the GUI elements and AR overlay may be configured to assist a user in acquiring corneal topography in a vertical orientation of a mobile device, as seen in FIG. 13. Beginning with FIG. 13A, a user may be instructed by a pop-up text window on how to orient the mobile phone with respect to the cornea indicating that the user will be acquiring data for a vertical aspect of corneal curvature. In some embodiments, the view of FIG. 13A may comprise a circular AR overlay that may be used by the user to position the distance and macroscopic alignment of the mobile device and camera sensor with respect to a displayed real-time image of the subject's eye and cornea. In some embodiments, sufficient alignment may occur when the circular AR overlay encompasses the cornea in its entirety, as shown in FIG. 13A. In some embodiments, the GUI view of FIG. 13A may also indicate to the user visually at the top of the view in a highlighted text window comprising a numeral of the step or portion of the total steps that is being conducted. In some embodiments, the user may then advance to acquiring data by tapping a large button with the indicator of "next". In some embodiments, the user may be shown the view, as can be seen in FIG. 13B, where the GUI comprises a set of text instructions and a circular GUI AR overlay element presented on a background of the image of what is in the field of view of the camera at the time the user has advanced to the view of FIG. 13B. In some embodiments, the circular GUI AR overlay element may comprise two-line elements separated by 180 degrees connected to the circular GUI AR overlay element in addition to a dotted line element traversing the vertical axis of the user's eye. In some embodiments, the two-line elements separated by 180 degrees connected to the circular GUI AR overlay element may be aligned with the dotted line element traversing the vertical length of the user's eye to properly align the mobile computing device to measure cornea curvature in the vertical plane. In some embodiments, the text instructions of FIG. 13B may inform the user that the user may need to rotate the body of the mobile computing device to align the camera sensor of the mobile computing device and the orientation of the horizontal axis of the subject's cornea. In some embodiments, upon rotating the mobile computing device to align the circular GUI AR elements shown in FIG. 13B, the user may then be presented with a view as seen in FIG. 13C. In some embodiments, the user may be presented with a circular GUI AR overlay element that may comprise two-line elements separated by 180 degrees connected to the circular GUI AR overlay element that is a different color than the circular GUI overlay element of FIG. 13B. In some embodiments, the circular GUI AR overlay element of a different color may be presented on a background of the image of what is in the field of view of the camera at the time the user has advanced to the view of FIG. 13C. In some embodiments, the user may also be presented with text notifying the user that the rotation of the mobile computing device has been properly set and that the user may proceed to capture a corneal curvature measurement. In some embodiments, the user may then be presented to view of FIG. 13D comprising a set of concentric colored circle GUI AR elements and text instructions. In some embodiments, the text instructions may describe to the user with a combination of text and graphic of how to move the set of concentric colored circular GUI AR elements to superimpose the concentric colored circular GUI AR elements on the user's iris as seen in FIG. 13D. In some embodiments, the user may then capture a corneal curvature measurement by tapping or pressing the capture button presented within the text field seen in FIG. 13D. In some embodiments, the user may then be presented with an illumination pattern seen in FIG. 13E.

In some embodiments, the GUI may comprise a marketplace where subjects may purchase contact lenses that are recommended based on the measured corneal diameter and corneal topography. In some embodiments, the marketplace may comprise a series of different windows with contact lens offerings from a plurality of vendors. In some embodiments, the marketplace GUI may comprise a set of customer's provided reviews and rating for the various contact lens offerings by a plurality of vendors Corneal topographic measurements can provide a rich dataset of diagnostic and prognostic factors that could greatly impact a subject's quality of life. For example, a subject interested in obtaining contact lenses, may have their corneal curvature measured by keratometry to ensure proper fit and function of the contact lens. Without proper measurement of a subject's cornea and fit of a contact lens, the subject may exhibit blurry vision or pain and potential damage to the subject's eye. Alternatively, corneal topographic measurements may be used as a preventive diagnostic screening tool or to monitor corneal surgical outcomes. To accurately and reproducibly measure the curvature of a subject's cornea, a robust and uniform light source is required. In some cases, the devices and systems of the disclosure provided herein may comprise a device configured to provide a uniform illumination.

In some cases, a uniform illumination source is critical when measuring the contour or topography of a surface. To appropriately measure surface contour or topography of the surface reproducibly and accurately, a structured illumination pattern should provide a constant spatial intensity i.e., uniform illumination. The uniformity of an illumination source may be determined by a ratio of the brightest region of intensity in a given field of the illumination source to the darkest region of a given filed of the illumination source. A ratio for a given illumination source that approaches a value of 1, indicates a uniform illumination source. Alternatively, the spatial distribution of light intensity of an illumination source may be used to describe a uniform illumination source. In some cases, the spatial gradient of the intensity generated by the illumination source in a field away from the illumination source may be utilized to describe the uniformity of an illumination source. In some instances, a uniform illumination source may comprise a spatial gradient change of up to about 30%, 20%, 10%, 5%, 1%, or less. A uniform illumination source with such a spatial intensity profile may increase the accuracy of an image or data processing method that determines a contour or topography of the surface by measuring a reflected light or light pattern from the surface. Such improvements in accuracy improve the reliability of such a processing method.

In some instances, the device may be configured to couple with a pre-existing light source. In some cases, the light source may be the light source of a smart-phone device. In some instances, the light source may be an independent light source. In some instances, the light source may comprise a light emitting diode (LED), super luminescent diode laser (SLD), laser, or any combination thereof. In some instances, the LED may be configured to output a spectrum of light, e.g., UV, Visible, NIR, or any combination thereof spectrum.

V. Uniform Panel Illuminator

Figure 15A:
FIGS. 15A-15B illustrate the top (FIG. 15A) and bottom (FIG. 15B) view of the uniform illumination panel, as described in some embodiments herein.
Figure 15A:
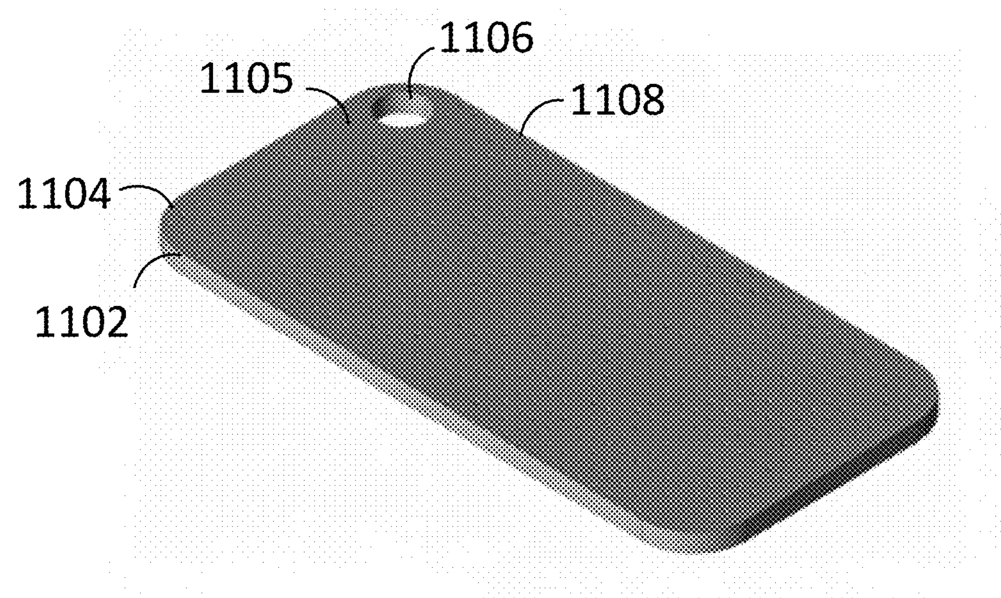
Figure 15B:
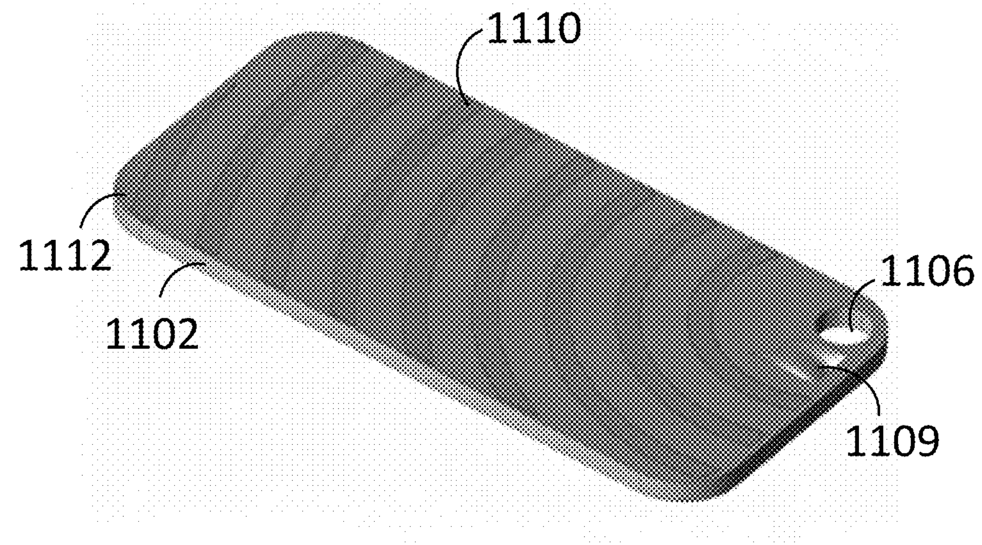
Figure 17:
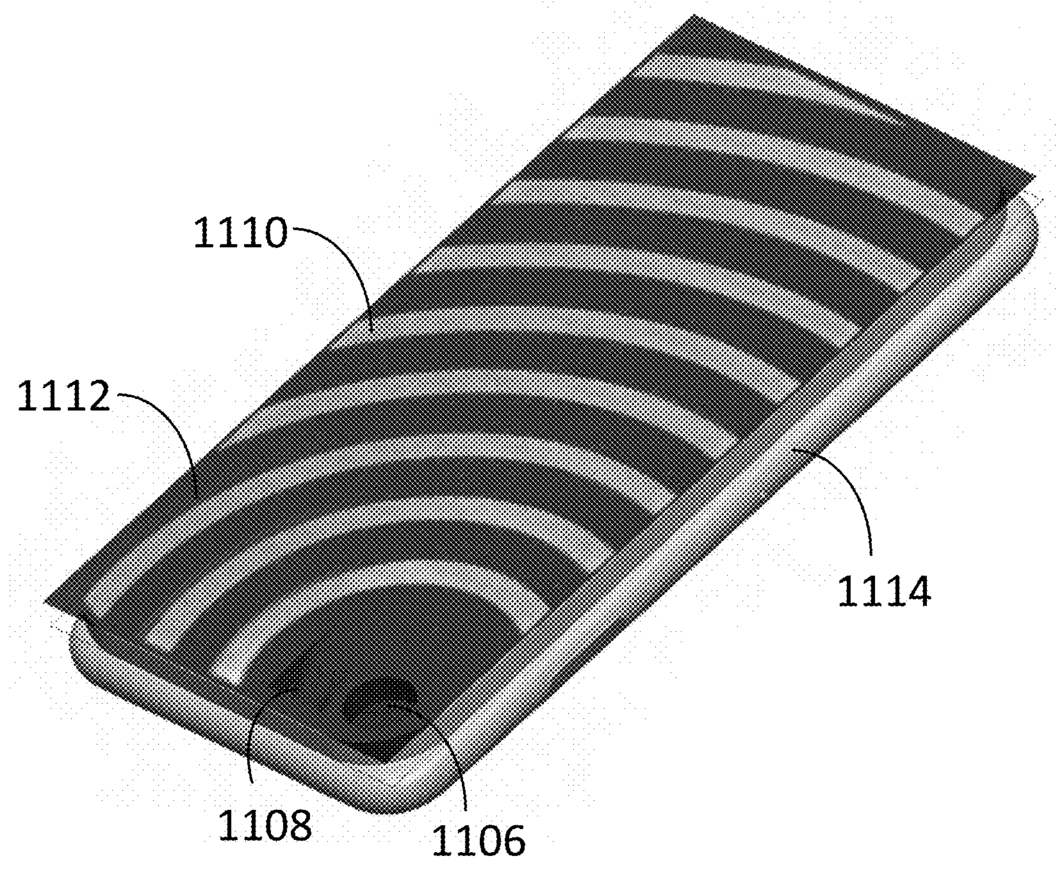
FIG. 17 illustrates a perspective view of the uniform illumination panel mounted on a smart phone, as described in some embodiments herein.
Figure 18A:
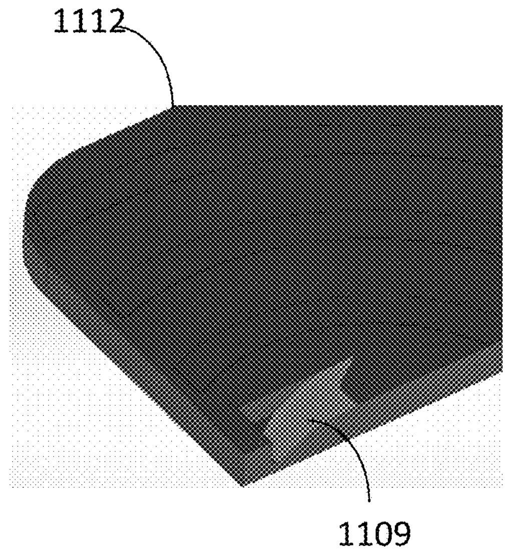
FIG. 18A-18B illustrate cross-sectional perspective views of the uniform illumination panel highlighting the curvature of the inlet waveguide, as described in some embodiments herein.
Figure 18B:
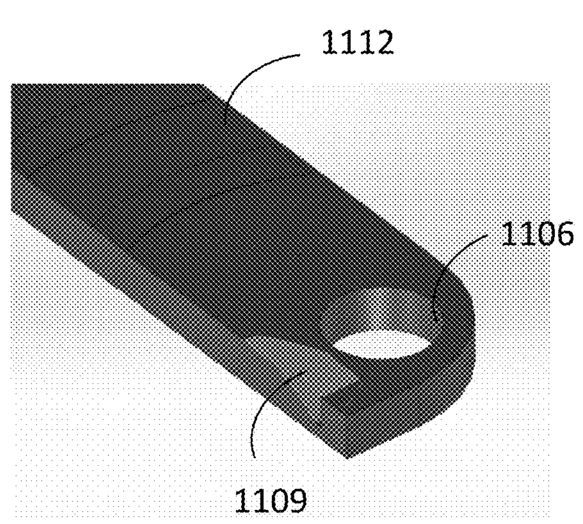

In some embodiments, the apparatus and systems of the disclosure provided herein may comprise an apparatus 1100 for illuminating a target, as seen in FIGS. 15A-15B. In some cases, the apparatus provides uniform illumination of the target uniformly to improve the determination of shape, spatial topography, and/or contour of the target. In some cases, uniform illumination comprises an illumination of one or more regions of the target such that a first region of the target has a brightness that is within about 10%, 9%, 8%, 6%, 4%, 2%, 1%, or less of a brightness of a second region of the target. In some cases, the brightness in region 1 is the same or similar to the brightness in region 2. In some instances, the target may comprise a biological tissue e.g., a corneal surface. In some instances, corneal surface may be a mammalian corneal surface. In some cases, the device may be configured to produce a uniform light source from a point light source. In some instances, the uniform light source may comprise a light source configured to provide an emitted illumination such that the emitted light source may comprise a constant or near constant brightness and/or intensity across an area, surface, field-of-view, or any combination thereof. In some cases, a point light source may comprise a light source of an electronic device. In some cases, the electronic device may comprise one or more individual light sources. In some instances, the one or more light sources may comprise an LED, SLD, laser, or any combination thereof. In some cases, the electronic device may comprise a smartphone. In some cases, the apparatus may be configured to be in optical communication with a smartphone 1114 light source, as seen in FIG. 17. In some cases, the device may comprise a panel that may be mechanically coupled to the smartphone 1114 via a case, shield, enclosure, partial enclosure, sleeve, or any combination thereof. In some cases, panel may comprise a quick release mechanism that enables the panel to be releasably coupled to the mobile device. In some instances, the quick release mechanism may enable coupling without the use of other tools. The coupling of the quick release mechanism may comprise a tension-based coupling of the panel to the smartphone 1114. In some instances, the quick release mechanism may comprise a snap-fit.

Turning to FIGS. 15A-15B, in some cases, the apparatus 1100 may comprise: (a) a first surface 1104 comprising one or more light scattering elements 1108 and (b) a second surface 1112 comprising a plurality of illumination elements 1110 in optical communication with the plurality of light scattering elements 1108, where the first surface 1104 comprises a light inlet 1109 comprising a curved surface or waveguide configured to (i) receive light emitted from a light source and (ii) direct the light to the one or more of light scattering elements. In some instances, the one or more of light scattering elements 1108 may be configured to transmit the light to the plurality of illumination elements 1110. In some cases, the plurality of illumination elements may be configured to generate a uniform illumination pattern for illuminating a target. In some cases, a surface of the apparatus may further comprise an optically transparent window 1105 in optical communication with the light source. In some instances, the apparatus may comprise an optically transparent window in optical communication with a sensor 1106. In some cases, the sensors may comprise a camera e.g., a smartphone camera, CMOS, CCD, or any combination thereof.

In some cases, the optically transparent window in optical communication with the sensor 106 may comprise a diameter of about 6 mm to about 15 mm. In some cases, the optically transparent window in optical communication with the sensor 1106 may comprise a diameter of about 6 mm to about 7 mm, about 6 mm to about 8 mm, about 6 mm to about 9 mm, about 6 mm to about 10 mm, about 6 mm to about 11 mm, about 6 mm to about 12 mm, about 6 mm to about 13 mm, about 6 mm to about 14 mm, about 6 mm to about 15 mm, about 7 mm to about 8 mm, about 7 mm to about 9 mm, about 7 mm to about 10 mm, about 7 mm to about 11 mm, about 7 mm to about 12 mm, about 7 mm to about 13 mm, about 7 mm to about 14 mm, about 7 mm to about 15 mm, about 8 mm to about 9 mm, about 8 mm to about 10 mm, about 8 mm to about 11 mm, about 8 mm to about 12 mm, about 8 mm to about 13 mm, about 8 mm to about 14 mm, about 8 mm to about 15 mm, about 9 mm to about 10 mm, about 9 mm to about 11 mm, about 9 mm to about 12 mm, about 9 mm to about 13 mm, about 9 mm to about 14 mm, about 9 mm to about 15 mm, about 10 mm to about 11 mm, about 10 mm to about 12 mm, about 10 mm to about 13 mm, about 10 mm to about 14 mm, about 10 mm to about 15 mm, about 11 mm to about 12 mm, about 11 mm to about 13 mm, about 11 mm to about 14 mm, about 11 mm to about 15 mm, about 12 mm to about 13 mm, about 12 mm to about 14 mm, about 12 mm to about 15 mm, about 13 mm to about 14 mm, about 13 mm to about 15 mm, or about 14 mm to about 15 mm. In some cases, the optically transparent window in optical communication with a sensor may comprise a diameter of about 6 mm, about 7 mm, about 8 mm, about 9 mm, about 10 mm, about 11 mm, about 12 mm, about 13 mm, about 14 mm, or about 15 mm. In some cases, the optically transparent window in optical communication with the sensor 1106 may comprise a diameter of at least about 6 mm, about 7 mm, about 8 mm, about 9 mm, about 10 mm, about 11 mm, about 12 mm, about 13 mm, or about 14 mm. In some cases, the optically transparent window in optical communication with the sensor 1106 may comprise a diameter of at most about 7 mm, about 8 mm, about 9 mm, about 10 mm, about 11 mm, about 12 mm, about 13 mm, about 14 mm, or about 15 mm.

In some instances, the apparatus may comprise a length of about 100 mm to about 180 mm. In some instances the apparatus may comprise a length of about 100 mm to about 110 mm, about 100 mm to about 120 mm, about 100 mm to about 130 mm, about 100 mm to about 140 mm, about 100 mm to about 150 mm, about 100 mm to about 160 mm, about 100 mm to about 170 mm, about 100 mm to about 180 mm, about 110 mm to about 120 mm, about 110 mm to about 130 mm, about 110 mm to about 140 mm, about 110 mm to about 150 mm, about 110 mm to about 160 mm, about 110 mm to about 170 mm, about 110 mm to about 180 mm, about 120 mm to about 130 mm, about 120 mm to about 140 mm, about 120 mm to about 150 mm, about 120 mm to about 160 mm, about 120 mm to about 170 mm, about 120 mm to about 180 mm, about 130 mm to about 140 mm, about 130 mm to about 150 mm, about 130 mm to about 160 mm, about 130 mm to about 170 mm, about 130 mm to about 180 mm, about 140 mm to about 150 mm, about 140 mm to about 160 mm, about 140 mm to about 170 mm, about 140 mm to about 180 mm, about 150 mm to about 160 mm, about 150 mm to about 170 mm, about 150 mm to about 180 mm, about 160 mm to about 170 mm, about 160 mm to about 180 mm, or about 170 mm to about 180 mm. In some instances, the apparatus may comprise a length of about 100 mm, about 110 mm, about 120 mm, about 130 mm, about 140 mm, about 150 mm, about 160 mm, about 170 mm, or about 180 mm. In some instances, the apparatus may comprise a length of at least about 100 mm, about 110 mm, about 120 mm, about 130 mm, about 140 mm, about 150 mm, about 160 mm, or about 170 mm. In some instances, the apparatus may comprise a length of at most about 110 mm, about 120 mm, about 130 mm, about 140 mm, about 150 mm, about 160 mm, about 170 mm, or about 180 mm.

In some cases, the apparatus may comprise a width of about 40 mm to about 120 mm. In some cases, the apparatus may comprise a width of about 40 mm to about 50 mm, about mm to about 60 mm, about 40 mm to about 70 mm, about 40 mm to about 80 mm, about 40 mm to about 90 mm, about 40 mm to about 100 mm, about 40 mm to about 110 mm, about 40 mm to about 120 mm, about 50 mm to about 60 mm, about 50 mm to about mm, about 50 mm to about 80 mm, about 50 mm to about 90 mm, about 50 mm to about 100 mm, about 50 mm to about 110 mm, about 50 mm to about 120 mm, about 60 mm to about 70 mm, about 60 mm to about 80 mm, about 60 mm to about 90 mm, about mm to about 100 mm, about 60 mm to about 110 mm, about 60 mm to about 120 mm, about 70 mm to about 80 mm, about 70 mm to about 90 mm, about 70 mm to about 100 mm, about 70 mm to about 110 mm, about 70 mm to about 120 mm, about 80 mm to about 90 mm, about 80 mm to about 100 mm, about 80 mm to about 110 mm, about 80 mm to about 120 mm, about 90 mm to about 100 mm, about 90 mm to about 110 mm, about 90 mm to about 120 mm, about 100 mm to about 110 mm, about 100 mm to about 120 mm, or about 110 mm to about 120 mm. In some cases, the apparatus may comprise a width of about 40 mm, about 50 mm, about 60 mm, about 70 mm, about 80 mm, about 90 mm, about 100 mm, about 110 mm, or about 120 mm. In some cases, the apparatus may comprise a width of at least about 40 mm, about 50 mm, about 60 mm, about 70 mm, about 80 mm, about 90 mm, about 100 mm, or about 110 mm. In some cases, the apparatus may comprise a width of at most about 50 mm, about 60 mm, about 70 mm, about 80 mm, about 90 mm, about 100 mm, about 110 mm, or about 120 mm.

In some instances, the apparatus may comprise a thickness of about 0.5 mm to about 6 mm. In some instances, the apparatus may comprise a thickness of about 0.5 mm to about 1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 0.5 mm to about 4.5 mm, about 0.5 mm to about 5 mm, about mm to about 5.5 mm, about 0.5 mm to about 6 mm, about 1 mm to about 1.5 mm, about 1 mm to about 2 mm, about 1 mm to about 2.5 mm, about 1 mm to about 3 mm, about 1 mm to about 3.5 mm, about 1 mm to about 4 mm, about 1 mm to about 4.5 mm, about 1 mm to about 5 mm, about 1 mm to about 5.5 mm, about 1 mm to about 6 mm, about 1.5 mm to about 2 mm, about 1.5 mm to about 2.5 mm, about 1.5 mm to about 3 mm, about 1.5 mm to about 3.5 mm, about 1.5 mm to about 4 mm, about 1.5 mm to about 4.5 mm, about 1.5 mm to about 5 mm, about 1.5 mm to about 5.5 mm, about 1.5 mm to about 6 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 5.5 mm, about 2 mm to about 6 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 5.5 mm, about 2.5 mm to about 6 mm, about 3 mm to about 3.5 mm, about 3 mm to about 4 mm, about 3 mm to about 4.5 mm, about 3 mm to about 5 mm, about 3 mm to about 5.5 mm, about 3 mm to about 6 mm, about 3.5 mm to about 4 mm, about 3.5 mm to about 4.5 mm, about 3.5 mm to about 5 mm, about 3.5 mm to about 5.5 mm, about 3.5 mm to about 6 mm, about 4 mm to about 4.5 mm, about 4 mm to about 5 mm, about 4 mm to about 5.5 mm, about 4 mm to about 6 mm, about 4.5 mm to about 5 mm, about 4.5 mm to about 5.5 mm, about 4.5 mm to about 6 mm, about 5 mm to about 5.5 mm, about 5 mm to about 6 mm, or about 5.5 mm to about 6 mm. In some instances, the apparatus may comprise a thickness of about 0.5 mm, about 1 mm, about 1.5 mm, about 2 mm, about 2.5 mm, about 3 mm, about 3.5 mm, about 4 mm, about 4.5 mm, about 5 mm, about 5.5 mm, or about 6 mm. In some instances, the apparatus may comprise a thickness of at least about 0.5 mm, about 1 mm, about 1.5 mm, about 2 mm, about 2.5 mm, about 3 mm, about 3.5 mm, about 4 mm, about 4.5 mm, about 5 mm, or about 5.5 mm. In some instances, the apparatus may comprise a thickness of at most about 1 mm, about 1.5 mm, about 2 mm, about 2.5 mm, about 3 mm, about 3.5 mm, about 4 mm, about 4.5 mm, about 5 mm, about 5.5 mm, or about 6 mm.

In some instances, the apparatus may have one or more fileted corners, as seen in FIGS. 15A-15B, and or straight edge corners. In some cases, the fileted corners may comprise a radius of about 8 mm to about 17 mm. In some cases, the fileted corners may comprise a radius of about 8 mm to about 9 mm, about 8 mm to about 10 mm, about 8 mm to about 11 mm, about 8 mm to about 12 mm, about 8 mm to about 13 mm, about 8 mm to about 14 mm, about 8 mm to about 15 mm, about 8 mm to about 16 mm, about 8 mm to about 17 mm, about 9 mm to about 10 mm, about 9 mm to about 11 mm, about 9 mm to about 12 mm, about 9 mm to about 13 mm, about 9 mm to about 14 mm, about 9 mm to about 15 mm, about 9 mm to about 16 mm, about 9 mm to about 17 mm, about 10 mm to about 11 mm, about 10 mm to about 12 mm, about 10 mm to about 13 mm, about 10 mm to about 14 mm, about 10 mm to about 15 mm, about 10 mm to about 16 mm, about 10 mm to about 17 mm, about 11 mm to about 12 mm, about 11 mm to about 13 mm, about 11 mm to about 14 mm, about 11 mm to about 15 mm, about 11 mm to about 16 mm, about 11 mm to about 17 mm, about 12 mm to about 13 mm, about 12 mm to about 14 mm, about 12 mm to about 15 mm, about 12 mm to about 16 mm, about 12 mm to about 17 mm, about 13 mm to about 14 mm, about 13 mm to about 15 mm, about 13 mm to about 16 mm, about 13 mm to about 17 mm, about 14 mm to about 15 mm, about 14 mm to about 16 mm, about 14 mm to about 17 mm, about 15 mm to about 16 mm, about 15 mm to about 17 mm, or about 16 mm to about 17 mm. In some cases, the fileted corners may comprise a radius of about 8 mm, about 9 mm, about 10 mm, about 11 mm, about 12 mm, about 13 mm, about 14 mm, about 15 mm, about 16 mm, or about 17 mm. In some cases, the fileted corners may comprise a radius of at least about 8 mm, about 9 mm, about 10 mm, about 11 mm, about 12 mm, about 13 mm, about 14 mm, about 15 mm, or about 16 mm. In some cases, the fileted corners may comprise a radius of at most about 9 mm, about 10 mm, about 11 mm, about 12 mm, about 13 mm, about 14 mm, about 15 mm, about 16 mm, or about 17 mm.

In some instances, the apparatus may comprise two or more surfaces 1102, 1104, and 1112, that may be configured to direct an input light source towards one or more illumination elements 1110. In some instances, the one or more surfaces may comprise a top 1104, bottom 1112, side 1102, or any combination thereof surface. The apparatus may comprise one or more surfaces (1104, 1102, 1112, and 1110) that may be transparent and/or translucent polished according to or in accordance with a polish standard, such as, for example, a society of plastic industry Al polish standard. In some cases, the one or more surfaces 1102, 1104, and 1112 may further comprise a reflective coating that may be applied to an unpolished and/or a polished surface. In some cases, the reflective coating may comprise a gold, silver, platinum, aluminum, polished stainless steel, chrome, or any combination thereof reflective coating. In some cases, the reflective may be configured to re-direct and/or re-distribute light coupled from a light source to the one or more light scattering elements to generate a uniform illumination source emitted at the illumination elements. In some cases, the reflective coating may provide the structural features similar to that of a laser cavity producing an emission with a relatively constant illumination both temporally and/or spatially. In some cases, the reflective coating may be configured to maximize internal reflection and brightness of the one or more illumination elements 1110. In some instances, the reflective coating may be configured to block or otherwise inhibit the propagation of emitted photons from the light source towards the subject's cornea.

In some instances, a surface 1112 of the one or more surfaces may comprise one or more illumination elements 1110 comprising one or more surfaces for illuminating a target or directing light to the target. In some instances, the one or more illumination elements 1110 produce a uniform illumination pattern that may be projected or directed to a target. In some cases, the illumination elements may provide a patterned illumination to determine a contour or topography of a surface. In some cases, the one or more illumination elements may be spatially arranged in a predetermined pattern. In some cases, the illumination elements 1110 may comprise a linear shape or profile, a non-linear shape or profile, or any combination thereof. In some cases, the non-linear shaped illumination elements may comprise a curve or an arc, as shown in FIG. 15B.

In some instances, the non-linear shaped illumination elements 1110 may comprise a radius of about 20 mm to about 170 mm. In some instances the non-linear shaped illumination elements 110 may comprise a radius of about 20 mm to about 40 mm, about mm to about 60 mm, about 20 mm to about 80 mm, about 20 mm to about 100 mm, about 20 mm to about 120 mm, about 20 mm to about 140 mm, about 20 mm to about 160 mm, about 20 mm to about 170 mm, about 40 mm to about 60 mm, about 40 mm to about mm, about 40 mm to about 100 mm, about 40 mm to about 120 mm, about 40 mm to about 140 mm, about 40 mm to about 160 mm, about 40 mm to about 170 mm, about 60 mm to about 80 mm, about 60 mm to about 100 mm, about 60 mm to about 120 mm, about 60 mm to about 140 mm, about 60 mm to about 160 mm, about 60 mm to about 170 mm, about 80 mm to about 100 mm, about 80 mm to about 120 mm, about 80 mm to about 140 mm, about 80 mm to about 160 mm, about 80 mm to about 170 mm, about 100 mm to about 120 mm, about 100 mm to about 140 mm, about 100 mm to about 160 mm, about 100 mm to about 170 mm, about 120 mm to about 140 mm, about 120 mm to about 160 mm, about 120 mm to about 170 mm, about 140 mm to about 160 mm, about 140 mm to about 170 mm, or about 160 mm to about 170 mm. In some instances, the non-linear shaped illumination elements 110 may comprise a radius of about 20 mm, about 40 mm, about 60 mm, about 80 mm, about 100 mm, about 120 mm, about 140 mm, about 160 mm, or about 170 mm. In some instances, the non-linear shaped illumination elements 1110 may comprise a radius of at least about 20 mm, about 40 mm, about 60 mm, about mm, about 100 mm, about 120 mm, about 140 mm, or about 160 mm. In some instances, the non-linear shaped illumination elements 1110 may comprise a radius of at most about 40 mm, about 60 mm, about 80 mm, about 100 mm, about 120 mm, about 140 mm, about 160 mm, or about 170 mm.

In some cases, the illumination elements may comprise a material with a refractive index of about 1.4 to about 2. In some cases, the illumination elements may comprise a material with a refractive index of about 1.4 to about 1.5, about 1.4 to about 1.6, about 1.4 to about 1.7, about 1.4 to about 1.8, about 1.4 to about 1.9, about 1.4 to about 2, about 1.5 to about 1.6, about 1.5 to about 1.7, about 1.5 to about 1.8, about 1.5 to about 1.9, about 1.5 to about 2, about 1.6 to about 1.7, about 1.6 to about 1.8, about 1.6 to about 1.9, about 1.6 to about 2, about 1.7 to about 1.8, about 1.7 to about 1.9, about 1.7 to about 2, about 1.8 to about 1.9, about 1.8 to about 2, or about 1.9 to about 2. In some cases, the illumination elements may comprise a material with a refractive index of about 1.4, about 1.5, about 1.6, about 1.7, about 1.8, about 1.9, or about 2. In some cases, the illumination elements may comprise a material with a refractive index of at least about 1.4, about 1.5, about 1.6, about 1.7, about 1.8, or about 1.9. In some cases, the illumination elements may comprise a material with a refractive index of at most about 1.5, about 1.6, about 1.7, about 1.8, about 1.9, or about 2.

In some instances, the illumination elements may comprise a height or depth of about millimeters to about 4 millimeters. In some instances, the illumination elements may comprise a height or depth of about 0.1 millimeters to about 0.2 millimeters, about 0.1 millimeters to about 0.3 millimeters, about 0.1 millimeters to about 0.4 millimeters, about millimeters to about 0.5 millimeters, about 0.1 millimeters to about 1 millimeter, about millimeters to about 1.5 millimeters, about 0.1 millimeters to about 2 millimeters, about 0.1 millimeters to about 3 millimeters, about 0.1 millimeters to about 4 millimeters, about 0.2 millimeters to about 0.3 millimeters, about 0.2 millimeters to about 0.4 millimeters, about 0.2 millimeters to about 0.5 millimeters, about 0.2 millimeters to about 1 millimeter, about 0.2 millimeters to about 1.5 millimeters, about 0.2 millimeters to about 2 millimeters, about 0.2 millimeters to about 3 millimeters, about 0.2 millimeters to about 4 millimeters, about 0.3 millimeters to about 0.4 millimeters, about 0.3 millimeters to about 0.5 millimeters, about 0.3 millimeters to about 1 millimeter, about 0.3 millimeters to about 1.5 millimeters, about 0.3 millimeters to about 2 millimeters, about 0.3 millimeters to about 3 millimeters, about 0.3 millimeters to about 4 millimeters, about 0.4 millimeters to about 0.5 millimeters, about 0.4 millimeters to about 1 millimeter, about 0.4 millimeters to about 1.5 millimeters, about 0.4 millimeters to about 2 millimeters, about 0.4 millimeters to about 3 millimeters, about 0.4 millimeters to about 4 millimeters, about 0.5 millimeters to about 1 millimeter, about 0.5 millimeters to about 1.5 millimeters, about 0.5 millimeters to about 2 millimeters, about 0.5 millimeters to about 3 millimeters, about 0.5 millimeters to about 4 millimeters, about 1 millimeter to about 1.5 millimeters, about 1 millimeter to about 2 millimeters, about 1 millimeter to about 3 millimeters, about 1 millimeter to about 4 millimeters, about 1.5 millimeters to about 2 millimeters, about 1.5 millimeters to about 3 millimeters, about 1.5 millimeters to about 4 millimeters, about 2 millimeters to about 3 millimeters, about 2 millimeters to about 4 millimeters, or about 3 millimeters to about 4 millimeters. In some instances, the illumination elements may comprise a height or depth of about 0.1 millimeters, about 0.2 millimeters, about 0.3 millimeters, about 0.4 millimeters, about 0.5 millimeters, about 1 millimeter, about 1.5 millimeters, about 2 millimeters, about 3 millimeters, or about 4 millimeters. In some instances, the illumination elements may comprise a height or depth of at least about 0.1 millimeters, about 0.2 millimeters, about 0.3 millimeters, about 0.4 millimeters, about 0.5 millimeters, about 1 millimeter, about 1.5 millimeters, about 2 millimeters, or about 3 millimeters. In some instances, the illumination elements may comprise a height or depth of at most about 0.2 millimeters, about 0.3 millimeters, about 0.4 millimeters, about 0.5 millimeters, about 1 millimeter, about 1.5 millimeters, about 2 millimeters, about 3 millimeters, or about 4 millimeters.

Figure 19:
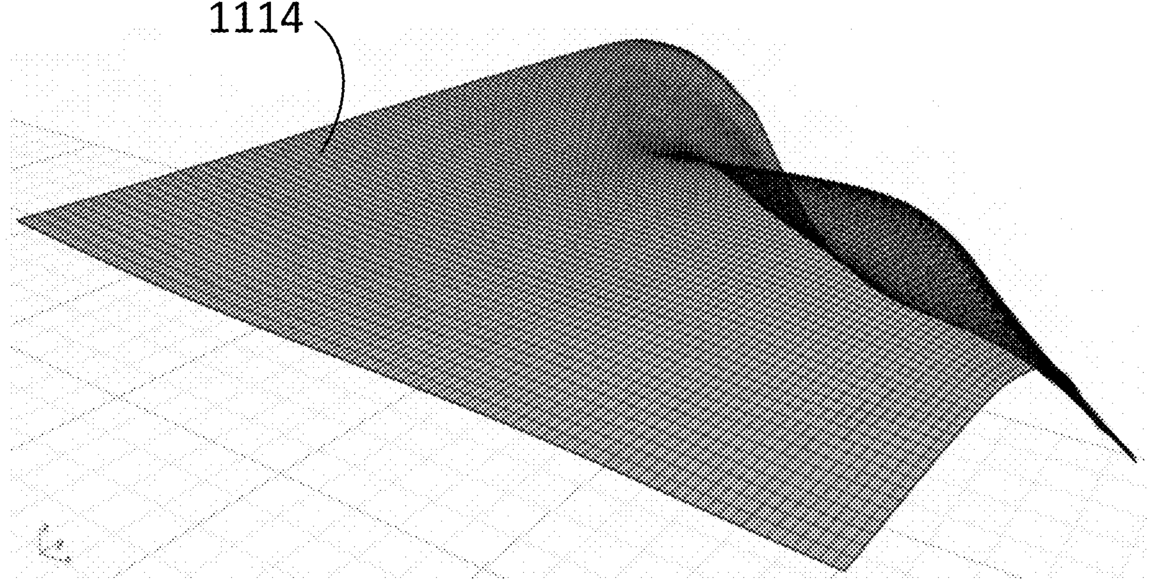
FIG. 19 illustrates the inlet waveguide curvature geometry model.

In some instances, apparatus may comprise a light inlet 1109. In some cases, the light inlet may comprise a curved surface or waveguide, as seen in FIG. 15B, FIGS. 18A-18B, and FIG. 19. The light inlet 1109 may comprise a curved surface 1114, as seen in FIG. 19. In some cases, the curved surface 1114 or waveguide may be configured to receive and distribute light from the light source to the plurality of light scattering elements while reducing or minimizing a light hot spot at or near the light inlet or the light source. In some instances, the light hot spot may correspond to or refer to a concentration of light at or near the light inlet 1109. In some cases, the refractive index of the light inlet 1109 may be a different refractive index than that of the apparatus. In some instances, the curved surface 1114 may direct the light emitted by the light source towards the one or more light scattering elements and the plurality of illumination elements. In some cases, a geometry of the curved surface 1114 may be determined based on the geometry and light emission characters of the light source. For example, two light sources with varying etendue may require a variation of the curved surface geometry.

Figure 16:
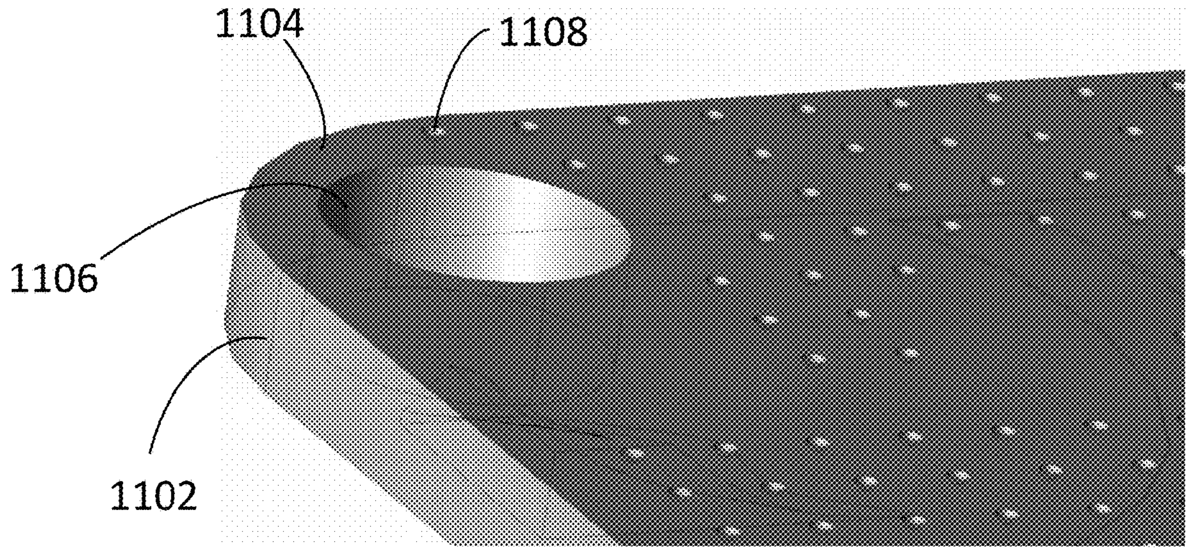
FIG. 16 illustrates a zoomed in perspective view of the bottom view of the uniform illumination panel, as described in some embodiments herein.

In some cases, the apparatus described herein may comprise one or more light scattering elements disposed on one of the first or second surfaces of the apparatus. In some instances, the one or more light scattering elements may comprise a two-dimensional array of light scattering elements arranged on a surface of the first or second surface, as can be seen in FIG. 15A and FIG. 16. In some instances, the two-dimensional array of the one or more light scattering elements may comprise a linear configuration, non-linear configuration, or any combination thereof. In some cases, the one or more light scattering elements may comprise one or more dome reflectors 1108, scattering particles, prisms, prisms, mirrors, dome reflectors, or any combination thereof.

In some cases, the curvature or composition of the light scattering elements may provide a geometric or light scattering re-distribution and/or re-direction of incident light onto the one or more scattering elements. In some instances, the one or more light scattering elements may isotopically scatter or re-distribute incident photons. In some instances, the light scattering elements may participate in Raleigh, Mie, or any combination thereof light scattering interactions. In some instances, the light scattering interaction with incident light may be determined by the difference in refractive index between the light scattering element and the surrounding medium.

The refractive index different between the light scattering element and the surround medium may comprise a refractive index difference of about 0.1 to about 2. The refractive index different between the light scattering element and the surround medium may comprise a refractive index difference of about 0.1 to about 0.2, about 0.1 to about 0.3, about 0.1 to about 0.4, about 0.1 to about 0.5, about 0.1 to about 0.6, about 0.1 to about about 0.1 to about 0.8, about 0.1 to about 0.9, about 0.1 to about 1, about 0.1 to about 1.5, about 0.1 to about 2, about 0.2 to about 0.3, about 0.2 to about 0.4, about 0.2 to about about 0.2 to about 0.6, about 0.2 to about 0.7, about 0.2 to about 0.8, about 0.2 to about 0.9, about 0.2 to about 1, about 0.2 to about 1.5, about 0.2 to about 2, about 0.3 to about 0.4, about 0.3 to about 0.5, about 0.3 to about 0.6, about 0.3 to about 0.7, about 0.3 to about 0.8, about 0.3 to about 0.9, about 0.3 to about 1, about 0.3 to about 1.5, about 0.3 to about 2, about 0.4 to about 0.5, about 0.4 to about 0.6, about 0.4 to about 0.7, about 0.4 to about 0.8, about 0.4 to about 0.9, about 0.4 to about 1, about 0.4 to about 1.5, about 0.4 to about 2, about 0.5 to about 0.6, about 0.5 to about 0.7, about 0.5 to about 0.8, about 0.5 to about 0.9, about 0.5 to about 1, about 0.5 to about 1.5, about 0.5 to about 2, about 0.6 to about 0.7, about 0.6 to about 0.8, about 0.6 to about 0.9, about 0.6 to about 1, about 0.6 to about 1.5, about 0.6 to about 2, about 0.7 to about 0.8, about 0.7 to about 0.9, about 0.7 to about 1, about 0.7 to about 1.5, about 0.7 to about 2, about 0.8 to about 0.9, about 0.8 to about 1, about 0.8 to about 1.5, about 0.8 to about 2, about 0.9 to about 1, about 0.9 to about 1.5, about 0.9 to about 2, about 1 to about 1.5, about 1 to about 2, or about 1.5 to about 2. The refractive index different between the light scattering element and the surround medium may comprise a refractive index difference of about 0.1, about 0.2, about 0.3, about 0.4, about 0.5, about 0.6, about 0.7, about 0.8, about 0.9, about 1, about 1.5, or about 2. The refractive index different between the light scattering element and the surround medium may comprise a refractive index difference of at least about 0.1, about about 0.3, about 0.4, about 0.5, about 0.6, about 0.7, about 0.8, about 0.9, about 1, or about 1.5. The refractive index different between the light scattering element and the surround medium may comprise a refractive index difference of at most about 0.2, about about 0.4, about 0.5, about 0.6, about 0.7, about 0.8, about 0.9, about 1, about 1.5, or about 2.

In some cases, the light scattering elements may comprise a geometry configured to re-direct or re-distribute incident photons in all or a subset thereof spherical vector trajectories of reflected or scattered light between the incident light and the one or more light scattering elements. The one or more light scattering elements may diffuse and/or re-distribute light in a way to generate uniform illumination source from a light source that may comprise a non-uniform illumination source. In some cases, the geometry and location of the light inlet 1109 may be designed in consideration of the position of the light source.

In some instances, the domed reflectors 1108 may comprise a radius of about 0.1 mm to about 1.5 mm. In some instances, the domed reflectors 108 may comprise a radius of about 0.1 mm to about 0.2 mm, about 0.1 mm to about 0.3 mm, about 0.1 mm to about 0.4 mm, about 0.1 mm to about 0.5 mm, about 0.1 mm to about 0.6 mm, about 0.1 mm to about 0.7 mm, about 0.1 mm to about 0.8 mm, about 0.1 mm to about 0.9 mm, about 0.1 mm to about 1 mm, about 0.1 mm to about 1.2 mm, about 0.1 mm to about 1.5 mm, about mm to about 0.3 mm, about 0.2 mm to about 0.4 mm, about 0.2 mm to about 0.5 mm, about 0.2 mm to about 0.6 mm, about 0.2 mm to about 0.7 mm, about 0.2 mm to about 0.8 mm, about 0.2 mm to about 0.9 mm, about 0.2 mm to about 1 mm, about 0.2 mm to about 1.2 mm, about 0.2 mm to about 1.5 mm, about 0.3 mm to about 0.4 mm, about 0.3 mm to about 0.5 mm, about 0.3 mm to about 0.6 mm, about 0.3 mm to about 0.7 mm, about 0.3 mm to about 0.8 mm, about 0.3 mm to about 0.9 mm, about 0.3 mm to about 1 mm, about mm to about 1.2 mm, about 0.3 mm to about 1.5 mm, about 0.4 mm to about 0.5 mm, about 0.4 mm to about 0.6 mm, about 0.4 mm to about 0.7 mm, about 0.4 mm to about 0.8 mm, about 0.4 mm to about 0.9 mm, about 0.4 mm to about 1 mm, about 0.4 mm to about 1.2 mm, about 0.4 mm to about 1.5 mm, about 0.5 mm to about 0.6 mm, about 0.5 mm to about 0.7 mm, about 0.5 mm to about 0.8 mm, about 0.5 mm to about 0.9 mm, about 0.5 mm to about 1 mm, about 0.5 mm to about 1.2 mm, about 0.5 mm to about 1.5 mm, about mm to about 0.7 mm, about 0.6 mm to about 0.8 mm, about 0.6 mm to about 0.9 mm, about 0.6 mm to about 1 mm, about 0.6 mm to about 1.2 mm, about 0.6 mm to about 1.5 mm, about 0.7 mm to about 0.8 mm, about 0.7 mm to about 0.9 mm, about 0.7 mm to about 1 mm, about 0.7 mm to about 1.2 mm, about 0.7 mm to about 1.5 mm, about 0.8 mm to about 0.9 mm, about 0.8 mm to about 1 mm, about 0.8 mm to about 1.2 mm, about mm to about 1.5 mm, about 0.9 mm to about 1 mm, about 0.9 mm to about 1.2 mm, about 0.9 mm to about 1.5 mm, about 1 mm to about 1.2 mm, about 1 mm to about 1.5 mm, or about 1.2 mm to about 1.5 mm. In some instances, the domed reflectors 1108 may comprise a radius of about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.2 mm, or about 1.5 mm. In some instances, the domed reflectors 1108 may comprise a radius of at least about 0.1 mm, about 0.2 mm, about 0.3 mm, about 0.4 mm, about 0.5 mm, about 0.6 mm, about 0.7 mm, about 0.8 mm, about 0.9 mm, about 1 mm, or about 1.2 mm. In some instances, the domed reflectors 108 may comprise a radius of at most about mm, about 0.3 mm, about 0.4 mm, about 0.5 mm, about 0.6 mm, about 0.7 mm, about mm, about 0.9 mm, about 1 mm, about 1.2 mm, or about 1.5 mm.

In some cases, the domed reflectors 1108 may comprise a depth of about 0.1 mm to about 1.5 mm. In some cases, the domed reflectors 108 may comprise a depth of about 0.1 mm to about 0.2 mm, about 0.1 mm to about 0.3 mm, about 0.1 mm to about 0.4 mm, about 0.1 mm to about 0.5 mm, about 0.1 mm to about 0.6 mm, about 0.1 mm to about 0.7 mm, about 0.1 mm to about 0.8 mm, about 0.1 mm to about 0.9 mm, about 0.1 mm to about 1 mm, about 0.1 mm to about 1.2 mm, about 0.1 mm to about 1.5 mm, about 0.2 mm to about 0.3 mm, about 0.2 mm to about 0.4 mm, about 0.2 mm to about 0.5 mm, about 0.2 mm to about 0.6 mm, about 0.2 mm to about 0.7 mm, about 0.2 mm to about 0.8 mm, about 0.2 mm to about 0.9 mm, about 0.2 mm to about 1 mm, about 0.2 mm to about 1.2 mm, about 0.2 mm to about 1.5 mm, about 0.3 mm to about 0.4 mm, about 0.3 mm to about 0.5 mm, about 0.3 mm to about 0.6 mm, about 0.3 mm to about 0.7 mm, about 0.3 mm to about 0.8 mm, about 0.3 mm to about 0.9 mm, about 0.3 mm to about 1 mm, about mm to about 1.2 mm, about 0.3 mm to about 1.5 mm, about 0.4 mm to about 0.5 mm, about 0.4 mm to about 0.6 mm, about 0.4 mm to about 0.7 mm, about 0.4 mm to about 0.8 mm, about 0.4 mm to about 0.9 mm, about 0.4 mm to about 1 mm, about 0.4 mm to about 1.2 mm, about 0.4 mm to about 1.5 mm, about 0.5 mm to about 0.6 mm, about 0.5 mm to about 0.7 mm, about 0.5 mm to about 0.8 mm, about 0.5 mm to about 0.9 mm, about 0.5 mm to about 1 mm, about 0.5 mm to about 1.2 mm, about 0.5 mm to about 1.5 mm, about mm to about 0.7 mm, about 0.6 mm to about 0.8 mm, about 0.6 mm to about 0.9 mm, about 0.6 mm to about 1 mm, about 0.6 mm to about 1.2 mm, about 0.6 mm to about 1.5 mm, about 0.7 mm to about 0.8 mm, about 0.7 mm to about 0.9 mm, about 0.7 mm to about 1 mm, about 0.7 mm to about 1.2 mm, about 0.7 mm to about 1.5 mm, about 0.8 mm to about 0.9 mm, about 0.8 mm to about 1 mm, about 0.8 mm to about 1.2 mm, about mm to about 1.5 mm, about 0.9 mm to about 1 mm, about 0.9 mm to about 1.2 mm, about 0.9 mm to about 1.5 mm, about 1 mm to about 1.2 mm, about 1 mm to about 1.5 mm, or about 1.2 mm to about 1.5 mm. In some cases, the domed reflectors 108 may comprise a depth of about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.2 mm, or about 1.5 mm. In some cases, the domed reflectors 1108 may comprise a depth of at least about 0.1 mm, about 0.2 mm, about 0.3 mm, about 0.4 mm, about 0.5 mm, about mm, about 0.7 mm, about 0.8 mm, about 0.9 mm, about 1 mm, or about 1.2 mm. In some cases, the domed reflectors 1108 may comprise a depth of at most about 0.2 mm, about 0.3 mm, about 0.4 mm, about 0.5 mm, about 0.6 mm, about 0.7 mm, about 0.8 mm, about 0.9 mm, about 1 mm, about 1.2 mm, or about 1.5 mm.

In some cases, the apparatus may be comprised of a material with a range of refractive index of about 1.49 to about 2 at 589.3 nanometers (nm). In some cases, the apparatus may comprise a material of polymethyl methacrylate (PMMA), acrylic, or any combination thereof.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the term "about" a number refers to that number plus or minus 10% of that number. The term "about" a range refers to that range minus 10% of its lowest value and plus 10% of its greatest value.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

Any systems, methods, software, compositions, and platforms described herein are modular and not limited to sequential steps. Accordingly, terms such as "first" and "second" do not necessarily imply priority, order of importance, or order of acts.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

What is claimed:

1. An apparatus for corneal topography measurement, comprising:

a panel configured to releasably couple to a mobile device, wherein the panel is further configured to (a) project a light pattern onto a cornea of an eye to generate a reflected light pattern and (b) aid transmission of the reflected light pattern from the cornea to an imaging device on the mobile device for generating a plurality of light signals, wherein an optical axis of the imaging device is offset from (i) a patterned region or (ii) an illumination source on the panel, wherein the panel comprises a plurality of curved scattering elements on a surface of the panel, and wherein the plurality of curved scattering elements reflects a light source to generate the projected light pattern.

2. The apparatus of claim 1, wherein the offset between the optical axis of the imaging device and the pattern region or the illumination source on the panel is from about 1 mm to about 10 mm.

3. The apparatus of claim 1, wherein the offset between the optical axis of the imaging device and the pattern region or the illumination source on the panel is from about 5 degrees to about 360 degrees.

4. The apparatus of claim 1, wherein the panel is configured to serve as a protective casing for the mobile device.

5. The apparatus of claim 1, wherein the panel light pattern comprises a plurality of lines.

6. The apparatus of claim 5, wherein the plurality of lines is linear.

7. The apparatus of claim 5, wherein the plurality of lines is circular or radial.

8. The apparatus of claim 1, wherein the panel comprises a quick release mechanism that enables the panel to be releasably coupled to the mobile device.

9. The apparatus of claim 8, wherein the quick release mechanism comprises a snap-fit.

10. The apparatus of claim 1, wherein the panel is transparent or translucent.

11. The apparatus of claim 1, wherein the panel has an absorption coefficient of about 1 cm^−1 to about 10 cm^−1.

12. The apparatus of claim 5, wherein the plurality of lines is opaque.

13. A system comprising:

the apparatus of claim 1; and one or more processors configured to process the plurality of light signals by (i) comparing the projected light pattern to the reflected light pattern to produce a two-dimensional elevation gradient, and (ii) using the two-dimensional elevation gradient to generate a three-dimensional topographic map of the cornea.

14. The system of claim 13, wherein the one or more processors are located on a server remote from the mobile device.

15. The system of claim 13, wherein the system further comprises the mobile device, and wherein the mobile device comprises a depth sensor configured to measure a distance from the cornea to the imaging device.

16. A method of measuring corneal topography, comprising:

(a) providing a panel having a plurality of lines and a plurality of curved scattering elements on a surface of the panel;

(b) coupling the panel to a mobile device in a configuration such that an optical axis of an imaging device on the mobile device is offset from a patterned region on the panel or an illumination source on the panel;

(c) placing the panel coupled to the mobile device in proximity to an eye of a subject;

(d) using the panel and the illumination source to project a light pattern onto the cornea to generate a reflected light pattern, wherein the plurality of curved scattering elements reflects the illumination source to generate the reflected light pattern;

(e) using the imaging device on the mobile device to receive the reflected light pattern to generate a plurality of light signals; and (f) generating a topography map of the cornea based at least in part on the plurality of light signals.

17. The method of claim 16, wherein (e) further comprises using a depth sensor on the mobile device to detect a distance between the panel and the eye of the subject.

18. The method of claim 16, wherein the plurality of lines on the panel is linear.

19. The method of claim 16, wherein the plurality of lines on the panel is circular or radial.

20. The method of claim 16, wherein (e) further comprises rotating the imaging device as the imaging device is receiving the reflected light pattern.

* * * * *